US006660496B1

(12) United States Patent
Pasternak et al.

(10) Patent No.: US 6,660,496 B1
(45) Date of Patent: *Dec. 9, 2003

(54) NUCLEIC ACID MOLECULES ENCODING A KOR3 KAPPA OPIOID RECEPTOR AND THE METHODS OF PRODUCING THE ENCODED RECEPTOR

(75) Inventors: Gavril W. Pasternak, New York, NY (US); Ying-Xian Pan, New York, NY (US)

(73) Assignee: Sloan-Kettering Institute for Cancer Research, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/986,209

(22) Filed: Dec. 5, 1997

Related U.S. Application Data

(63) Continuation of application No. 08/147,949, filed on Nov. 5, 1993, now Pat. No. 5,747,279.

(51) Int. Cl.[7] .......................... C12P 21/06; C12N 1/20; C12N 15/74; C07H 21/04
(52) U.S. Cl. ................ 435/69.1; 435/252.3; 435/320.1; 435/471; 536/23.5
(58) Field of Search ....................... 536/23.5; 435/69.1, 435/320.1, 70.1, 71.1, 71.2, 252.3, 325, 471

(56) References Cited

U.S. PATENT DOCUMENTS 5,747,279 A   5/1998  Pasternak et al. .......... 435/69.1
6,096,513 A * 8/2000  Bell et al.

OTHER PUBLICATIONS

Lewin, Science, 237, 1570, Sep. 25, 1987.*
Reeck, Cell, 50, 667, Aug. 28, 1987.*
Cheng et al., European Journal of Pharmacology, 226, 15–20, 1992.*
Evans et al., Science, 258, 1952–1955, Dec. 19, 1992.*
Breder, C.D., et al. (1992) "Differential expression of somatostatin receptor subtypes in brain", *J. Neurosci.* 12:3920–3934.
Chen, Y. et al. (1994) "Molecular Cloning, Tissue Distribution and Chromosomal Localization of a Novel Member of the Opioid Receptor Gene Family," *Federation of European Biochemical Societies* 347:279–293. (Exhibit C).
Chen, Y. et al. (1993) "Molecular Cloning of a Rat $_k$ Opioid Receptor Reveals Sequence Similarites to the $\mu$ and $\delta$ Opioid Receptors," *Biochem. J.* 295:625–628. (Exhibit D).

Clark, J.A., et al. (1989) "Kappa opiate receptor muultiplicity: Evidence for two U50, 488–sensitive $K_1$ subtypes and a novel $K_3$ subtype", *J. Pharmacol. Expt. Therapeut*, 251:461–468.
Cotecchia, S., et al. (1988) "Molecular cloning and expression of the cDNA for the hamster $\alpha_1$–adrenergic receptor", *Proc. Natl. Acad. Sci. USA* 85:7159–7163.
Dohlman, H.G., et al. (1987) "A family of receptors coupled to guanine nucleotide regulatory proteins", *Biochemsitry* 26:2657–2664.
Gioannini, T.L., et al. (1989) "Evidence for the presence of disulfide bridges in opioid receptors essential for ligand binding. Possible role in receptor activation", *J. Mol. Recogn.* 2:44–48.
King, K., et al. (1990) "Control of yeast mating signal transduction by a mammalian $\beta_2$–adrenergic receptor and $G_s$ $\alpha$subunit", *Science* 250:121–123.
Kobilka, B.K., et al. (1987) "Delineation of the intronless nature of the genes for the human and hamster $\beta_2$–adrenergic receptor and their putative promoter regions", *J. Biol. Chem.* 262:7321–7327.
Lomansey, J.W., et al. (1990) "Expansion of the $\alpha_2$–adrenergic receptor family: Cloning and characterization of a human $\alpha_2$–adrenergic receptor subtype, the gene for which is located on chromosome 2", *Proc. Natl. Acad. Sci. USA* 87:5094–5098.
Lutz, R.A. and Pfister, H.P. (1992) "Opioid receptors and their pharmacological profiles", *J. Receptor Res.* 12:267–286.
Marullo, S., et al. (1988) "Human $\beta_2$–adrenergic receptors expressed in *Escherichia coli* membranes retain their pharmacological properties", *Proc. Natl. Acad. Sci. USA* 85:7551–7555.
Olson, G.A., et al. (1989) "Endogenous Opiates: 1988", *Peptides* 10:1253–1280.

(List continued on next page.)

*Primary Examiner*—Robert S. Landsman
(74) *Attorney, Agent, or Firm*—Frommer, Lawrence & Haug LLP; William F. Lawrence; Amy Leahy

(57) ABSTRACT

The subject invention provides recombinant nucleic acid molecule which encodes a kappa$_3$ opioid receptor, and the receptor encoded thereby. The subject invention further provides related anti-sense oligonucleotide molecules. The subject invention further provides a related host vector system, and method for using same. The subject invention further provides polyclonal and monoclonal antibodies capable of specifically binding to kappa$_3$ opioid receptor, methods for obtaining same, and methods of using same to detect the presence of, and quantitatively determine the amount of, kappa$_3$ opioid receptor in a sample, image and quantitatively determine the amount of cell membrane-bound kappa$_3$ opioid receptor present in a subject, determine a subject's potential sensitivity to a kappa$_3$ opioid receptor-specific agent, determine the affinity of an agent for kappa$_3$ opioid receptor, and identify agonists and antagonists of kappa$_3$ opioid receptor.

23 Claims, 5 Drawing Sheets

OTHER PUBLICATIONS

Pert, C.B. and Snyder S.H. (1973) "Opiate receptor: demonstration in nervous tissue", *Science* 179:1011–1014.

Regan, J.W., et al. (1988) "Cloning and expression of a human kidney cDNA for an $\alpha_2$–adrenergic receptor subtype", *Proc. Natl. Acad. Sci. USA* 85:6301–6305.

Xie, G–X., et al. (1992) "Expression cloning of cDNA encoding a seven–helix receptor from human placenta with affinity for opioid ligands", *Proc. Natl. Acad. Sci. USA* 89:4124–4128.

* cited by examiner

FIG. 1A

```
         10         20         30         40         50         60
TTTGGCTTCCTTCTCCAACCTGCGCAGCCCCTCCTTCTCTCAGCCGCAGCCTTCTGCCCC
         70         80         90        100        110        120
TCCCCCTTCTGGCTGCCGCACTGGCTGCTGCGTCTAGTCAATATCTTATCTTCGGAGCAG
        130        140        150        160        170        180
GAGCTAGGAGCCATTCCCAGCCGGAGCAGACCCCAAGCTAGAGTGAGAAGCATTACTCAG
        190        200        210        220        230        240
TTCATTGTGCTCCTGCCTGCCTTTCTGCTAAGCATTAGGGTCTGTTTTGGCCCAGCTTCT
        250        260        270        280        290        300
GAAGAGGTTGTGTGTGCTGTTGGAGGAACTGTACTGAGTGGCTTTGCAGGGTGACAGCAT
                                                               M 310        320        330        340        350        360
GGAGTCCCTCTTTCCTGCCCCATTCTGGGAGGTCTTGTATGGCAGCCACTTTCAAGGGAA
  E    S    L    F    P    A    P    F    W    E    V    L    Y    G    S    H    F    Q    G    N 370        380        390        400        410        420
CCTGTCTCTCCTAAATGAGACCGTACCCCATCACCTGCTCCTCAATGCTAGCCACAGTGC
  L    S    L    L    N    E    T    V    P    H    H    L    L    N    A    S    H    S    A 430        440        450        460        470        480
CTTCCTGCCCCTTGGACTCAAGGTCACCATCGTGGGGCTCTACTTGGCTGTGTGCATCGG
  F    L    P    L    G    L    K    V    T    I    V    G    L    Y    L    A    V    C    I    G 490        500        510        520        530        540
GGGGCTCCTGGGGAACTGCCTCGTCATGTATGTCATCCTCAGGCACACCAAGATGAAGAC
  G    L    L    G    N    C    L    V    M    Y    V    I    L    R    H    T    K    M    K    T 550        560        570        580        590        600
TGCTACCAACATTTACATATTTAATCTGGCACTGGCTGATACCCTGGTCTTGCTGACACT
  A    T    N    I    Y    I    F    N    L    A    L    A    D    T    L    V    L    L    T    L 610        620        630        640        650        660
GCCCTTCCAGGGCACAGACATCCTTCTGGGCTTCTGGCCATTTGGGAATGCACTGTGCAA
  P    F    Q    G    T    D    I    L    L    G    F    W    P    F    G    N    A    L    C    K 670        680        690        700        710        720
GACGGTCATTGCTATCGACTACTACAACATGTTTACCAGCACTTTCACTTTGACTGCCAT
  T    V    I    A    I    D    Y    Y    N    M    F    T    S    T    F    T    L    T    A    M 730        740        750        760        770        780
GAGTGTAGACCGTTATGTAGCTATCTGCCACCCTATCCGTGCCCTTGATGTTCGGACATC
  S    V    D    R    Y    V    A    I    C    H    P    I    R    A    L    D    V    R    T    S
```

FIG. 1B

```
         790       800       810       820       830       840
CAGTAAAGCCCAGGCCGTTAATGTGGCCATATGGGCCCTGGCTTCGGTGGTTGGTGTTCC
   S   K   A   Q   A   V   N   V   A   I   W   A   L   A   S   V   V   G   V   P 850       860       870       880       890       900
TGTTGCCATCATGGGCTCAGCACAAGTGGAGGATGAAGAGATCGAGTGCCTGGTGGAGAT
   V   A   I   M   G   S   A   Q   V   E   D   E   E   I   E   C   L   V   E   I 910       920       930       940       950       960
CCCCGCCCCTCAGGACTATTGGGGCCCTGTATTTGCCATCTGCATCTTCCTTTTTTCCTT
   P   A   P   Q   D   Y   W   G   P   V   F   A   I   C   I   F   L   F   S   F 970       980       990      1000      1010      1020
CATCATCCCGGTTCTGATCATCTCTGTCTGCTACAGCCTCATGATTCGACGACTTCGTGG
   I   I   P   V   L   I   I   S   V   C   Y   S   L   M   I   R   R   L   R   G 1030      1040      1050      1060      1070      1080
TGTCCGGCTGCTTTCAGGCTCCCGAGAGAAGGACCGGAACCTGCGACGCATCACACGGCT
   V   R   L   L   S   G   S   R   E   K   D   R   N   L   R   R   I   T   R   L 1090      1100      1110      1120      1130      1140
GGTACTGGTAGTTGTGGCTGTGTTTGTGGGCTGCTGGACACCTGTGCAGGTCTTTGTCCT
   V   L   V   V   V   A   V   F   V   G   C   W   T   P   V   Q   V   F   V   L 1150      1160      1170      1180      1190      1200
GGTTCAAGGACTGGGTGTTCAGCCAGGTAGTGAGACTGCAGTAGCCATTCTGCGCTTCTG
   V   Q   G   L   G   V   Q   P   G   S   E   T   A   V   A   I   L   R   F   C 1210      1220      1230      1240      1250      1260
CACAGCCCTGGGCTATGTCAACAGTTGTCTCAATCCCATTCTCTATGCTTTCTTGGATGA
   T   A   L   G   Y   V   N   S   C   L   N   P   I   L   Y   A   F   L   D   E 1270      1280      1290      1300      1310      1320
GAACTTCAAGGCCTGCTTTAGAAAGTTCTGCTGTGCTTCTGCCCTGCACCGGGAGATGCA
   N   F   K   A   C   F   R   K   F   C   C   A   S   A   L   H   R   E   M   Q 1330      1340      1350      1360      1370      1380
GGTTTCTGATCGTGTGCGCAGCATTGCCAAGGATGTAGGCCTTGGTTGCAAGACCTCTGA
   V   S   D   R   V   R   S   I   A   K   D   V   G   L   G   C   K   T   S   E 1390      1400      1410      1420      1430      1440
GACAGTACCACGGCCGGCATGACTAGGCGTGGACCTGCCCATGGTGCCTGTCAGTCCTAG
   T   V   P   R   P   A 1450      1460      1470      1480      1490      1500
AGGAAGACCTTTTAGCACCATGGGACAGGTCAAAGCATCAAGGTGGCCTCCATGGCTCTG
        1510      1520      1530      1540      1550      1560
TCAGATTAAGTTTCCTCCCTGGTATAGGACCAGAGAGAACCAAAGGAACTGCATGGAAAC
```

FIG. 1C

```
       1570       1580       1590       1600       1610       1620
ATCCACAACTCAGTGGACATGCCTGGTGAACCCATGTAGGTATTCATGGTTCACTTGACT
       1630       1640       1650       1660       1670       1680
CTTCTCTGGTTTCTCCCTGCTGCCCTGGTTCTAGGTGGGCTCAGCTGAGGTATTGTAGTT
       1690       1700       1710       1720       1730       1740
GTCATGTAGTCACTATTGTGACTACCTGTTGTGTGCTATTGCCCTCAGCCTTCAGTGTTT
       1750       1760       1770       1780       1790       1800
GCACAGAACTGGTGATCATACCCAGTGTTGCCTGGCCCTTAAGCTTGGAGTTGCCTTGGA
       1810       1820       1830       1840       1850       1860
GCATCTAGTTCTGACTCCACTGATGCATTCAGATTACCTGAGGTGGGTGAGCATCAGTGG
       1870       1880       1890       1900       1910       1920
GTTCTTGGATGACTGTTTCCTGACGATTCTTTTCATGCTGTACTATGGTGTATATGAAGG
       1930       1940       1950       1960       1970       1980
GGACTTCACACTTCATCTGGTACTGCCACTGCCTGCTCTACCAACCTGGACCACCTTCTC
       1990       2000       2010       2020       2030       2040
AGCAAGAGGCTAGCAGGGGACAAGACACAAAGCTTCCCTAAGGCTCTTTCCCTCCAAAA
       2050       2060       2070       2080       2090       2100
CCACTGTGAACTCTTATTCTACAGACTGTTTGGCAAGCCCTGCTTCTAACTGTGTGGGAA
       2110       2120       2130       2140       2150       2160
GTAATCAGGAGAAAATTCTGTGGCCTCTGTAGGCTGCTCACAGCATGGAGGCACCACATG
       2170       2180       2190       2200       2210       2220
CTGGTCTTGGGTATGTGTCTTGGCTGCTCAGTATGGGCAGGGCAGGGCACGAGACTATCT
       2230       2240       2250       2260       2270       2280
CTCTCCTTATTCTCCACAGCCTCCCTCAGCTCTCCAGCAGTCGCTCTTTTACTTGACAGT
       2290       2300       2310       2320       2330       2340
AGAGGTTAGCAGCAGTTGTACTCGTAGAAACACACTTGTAGCCCGGGAAGACTGGAGTCA
       2350       2360       2370       2380       2390       2400
GGATGTGTTCTATTCTATACCCACAGTGACCACCTGCTTCATTTATAGGGTTAGGACATA
       2410       2420       2430       2440       2450       2460
TCCAAGCAAGGCCTGGGCTTGGCATCAAATGAAGAGCTGGTATGAGAGCTGAAGCCTAAA
       2470       2480       2490       2500       2510       2520
ATGGCTCATTTGAGCAATCTGCAAGGACTATTACGGTTTTGGGGACATTGGAAGAAGAGT
```

FIG. 1D

```
         2530      2540      2550      2560      2570      2580
CGATACCTTGGAGATATATTGTTGGTTCACAGAAGAAGAGGCTTTGTAAATGCCCTTTCT
         2590      2600
ATGGGTCAGATAAAAAAAAA
```

NUCLEIC ACID MOLECULES ENCODING A KOR3 KAPPA OPIOID RECEPTOR AND THE METHODS OF PRODUCING THE ENCODED RECEPTOR

This application is a continuation of U.S. application Ser. No. 08/147,949, filed Nov. 5, 1993, now U.S. Pat. No. 5,747,279, the contents of which are hereby incorporated by reference.

This invention was made with support under Grant Nos. DA02615 RO1 and 1K02 DA00138 from the National Institute on Drug Abuse. Accordingly, the U.S. government has certain rights in the invention.

BACKGROUND OF THE INVENTION

Throughout this application, various publications are referenced. Full citations for these references may be found at the end of the specification immediately preceding the claims. The disclosure of these publications is hereby incorporated by reference into this application to describe more fully the art to which this invention pertains. Opioid drugs have various effects on perception of pain, consciousness, motor control, mood, and autonomic function and can also induce physical dependence (Koob, et al (1992)). The endogenous opioid system plays an important role in modulating endocrine, cardiovascular, respiratory, gastrointestinal and immune functions (Olson, et al (1989)). Opioids exert their actions by binding to specific membrane-associated receptors located throughout the central and peripheral nervous system (Pert, et al. (1973)). The endogenous ligands of these opioid receptors have been identified as a family of more than 20 opioid peptides that derive from the three precursor proteins proopiomelanocortin, proenkephalin, and prodynorphin (Hughes, et al. (1975); Akil, et al. (1984)). Although the opioid peptides belong to a class of molecules distinct from the opioid alkaloids, they share common structural features including a positive charge juxtaposed with an aromatic ring that is required for interaction with the receptor (Bradbury, et al. (1976)).

Pharmacological studies have suggested that there are at least three major classes of opioid receptors, designated $\delta$, $\kappa$, $\mu$ and $\sigma$ (Simon 1991; Lutz, et al. (1992)). The classes differ in their affinity for various opioid ligands and in their cellular distribution. The different classes of opioid receptors are believed to serve different physiological functions (Olson, et al., (1989); Simon (1991); Lutz & Pfister (1992)). However, there is substantial overlap of function as well as of distribution. Despite pharmacological and physiological heterogeneity, at least some types of opioid receptors inhibit adenylate cyclase, increase $K_+$ conductance, and inactivate $Ca^{2+}$ channels through a pertussis toxin-sensitive mechanism (Puttfarcken, et al. 1988; Attali, et al. 1989; Hsia, et al., 1984). These results and others suggest that opioid receptors belong to the large family of cell surface receptors that signal through G proteins (Di Chiara, et al. (1992); Loh, et al. (1990)).

Several attempts to clone cDNAs encoding opioid receptors have been reported. A cDNA encoding an opioid-binding protein (OBCAM) with $\mu$ selectivity was isolated (Schofield, et al. (1989)), but the predicted protein lacks transmembrane domains presumed necessary for signal transduction. More recently, the isolation of another cDNA was reported, which was obtained by expression cloning (Xie, et al. (1992)). The deduced protein sequence displays seven putative transmembrane domains and is very similar to the human neuromedin K receptor. However, the affinity of opioid ligands for this receptor expressed in COS cells is two orders of magnitude below the expected value, and no subtype selectivity can be shown.

Many cell surface receptor/transmembrane systems consist of at least three membrane-bound polypeptide components: (a) a cell-surface receptor; (b) an effector, such as an ion channel or the enzyme adenylate cyclase; and (c) a guanine nucleotide-binding regulatory polypeptide or G protein, that is coupled to both the receptor and its effector.

G protein-coupled receptors mediate the actions of extracellular signals as diverse as light, odorants, peptide hormones and neurotransmitters. Such receptors have been identified in organisms as evolutionarily divergent as yeast and man. Nearly all G protein coupled receptors bear sequence similarities with one another, and it is thought that all share a similar topological motif consisting of seven hydrophobic (and potentially a-helical) segments that span the lipid bilayer (Dohlman et al. (1987); Dohlman et al. (1991)).

G proteins consist of three tightly associated subunits, $\alpha$, $\beta$ and $\gamma$ (1:1:1) in order of decreasing mass. Following agonist binding to the receptor, a conformational change is transmitted to the G protein, which causes the G$\alpha$-subunit to exchange a bound GDP for GTP and to dissociate from the $\beta\gamma$-subunits. The GTP-bound form of the $\alpha$-subunit is typically the effector-modulating moiety. Signal amplification results from the ability of a single receptor to activate many G protein molecules, and from the stimulation by G$\alpha$-GTP of many catalytic cycles of the effector.

The family of regulatory G proteins comprises a multiplicity of different $\alpha$-subunits (greater than twenty in humans), which associate with a smaller pool of $\beta$- and $\gamma$-subunits (greater than four each) (Strothman and Simon (1991)). Thus, it is anticipated that differences in the $\alpha$-subunits probably distinguish the various G protein oligomers, although the targeting or function of the various $\alpha$-subunits might also depend on the $\beta\gamma$ subunits with which they associate (Strothman and Simon (1991).

Improvements in cell culture and in pharmacological methods, and more recently, use of molecular cloning and gene expression techniques have led to the identification and characterization of many seven-transmembrane segment receptors, including new sub-types and sub-sub-types of previously identified receptors. The $\alpha_1$ and $\alpha_2$-adrenergic receptors once thought to each consist of single receptor species, are now known to each be encoded by at least three distinct genes (Kobilka et al. (1987); Regan et al. (1988); Cotecchia et al. (1988); Lomasney (1990)). In addition to rhodopsin in rod cells, which mediates vision in dim light, three highly similar cone pigments mediating color vision have been cloned (Nathans et al. (1986)A; and Nathans et al. (1986)B). All of the family of G protein-coupled receptors appear to be similar to other members of the family of G protein-coupled receptors (e.g., dopaminergic, muscarinic, serotonergic, tachykinin), and each appears to share the characteristic seven-transmembrane segment topography.

When comparing the seven-transmembrane segment receptors with one another, a discernible pattern of amino acid sequence conservation is observed. Transmembrane domains are often the most similar, whereas the amino and carboxyl terminal regions and the cytoplasmic loop connecting transmembrane segments V and VI can be quite divergent (Dohlman et al. (1987)).

Interaction with cytoplasmic polypeptides, such as kinases and G proteins, was predicted to involve the hydrophobic loops connecting the transmembrane domains of the receptor. The challenge, however, has been to determine which features are preserved among the seven-transmembrane segment receptors because of conservation of function, and which divergent features represent structural adaptations to new functions. A number of strategies have been used to test these ideas, including the use of recombinant DNA and gene expression techniques for the construction of substitution and deletion mutants, as well as of hybrid or chimeric receptors (Dohlman et al. (1991)).

With the growing number of receptor sub-types, G-protein subunits, and effectors, characterization of ligand binding and G protein recognition properties of these receptors is an important area for investigation. It has long been known that multiple receptors can couple to a single G protein and, as in the case of epinephrine binding to $\beta_2$- and $\alpha_2$-adrenergic receptors, a single ligand can bind to multiple functionally distinct receptor sub-types. Moreover, G proteins with similar receptor and effector coupling specificities have also been identified. For example, three species of human $G_i$ have been cloned (Itoh et al. (1988)), and alternate mRNA splicing has been shown to result in multiple variants of $G_s$ (Kozasa et al. (1988)). Cloning and over production of the muscarinic and $\alpha_2$-adrenergic receptors led to the demonstration that a single receptor sub-type, when expressed at high levels in the cell, will couple to more than one type of G protein.

Opioid receptors are known to be sensitive to reducing agents, and the occurrence of a disulfide bridge has been postulated as essential for ligand binding (Gioannini, et al. (1989)). For rhodopsin, muscarinic, and $\beta$-adrenergic receptors, two conserved cysteine residues in each of the two first extracellular loops have been shown critical for stabilizing the functional protein structure and are presumed to do so by forming a disulfide bridge. Structure/function studies of opioid ligands have shown the importance of a protonated amine group for binding to the receptor with high affinity. The binding: site of the receptor might, therefore, possess a critical negatively charged counterpart. Catecholamine receptors display in their sequence a conserved aspartate residue that has been shown necessary for binding the positively charged amine group of their ligands.

Given the complexity and apparent degeneracy of function of various opioid receptors, a question of fundamental importance is how, and under what circumstances do specific sub-type and sub-sub-type receptors exert their physiological effect in the presence of the appropriate stimulatory ligand. A traditional approach to answering this question has been to reconstitute the purified receptor and G protein components in vitro. Unfortunately, purification schemes have been successful for only a very limited number of receptor sub-types and their cognate G-proteins. Alternatively, heterologous expression systems can be of more general usefulness in the characterization of cloned receptors and in elucidating receptor G protein coupling specificity (Marullo et al. (1988); Payette et al. (1990); King et al. (1990)).

One such system was recently developed in yeast cells, in which the genes for a mammalian $\beta_2$-adrenergic receptor and $G_s$ $\alpha$-subunit were coexpressed (King et al. 1990). Expression of the $\beta_2$-adrenergic receptor to levels several hundred-fold higher than in any human tissue was attained, and ligand binding was shown to be of the appropriate affinity, specificity, and stereoselectivity. Moreover, a $\beta_2$-adrenergic receptor-mediated activation of the pheromone signal transduction pathway was demonstrated by several criteria, including imposition of growth arrest, morphological changes, and induction of ia pheromone-responsive promoter (FUSI) fused to the *Escherichia coli* lacz gene (encoding $\beta$-galactosidase) (King et al. 1990).

Finally, expression of a single receptor in the absence of other related sub-types is often impossible to achieve, even in isolated, non-recombinant mammalian cells. Thus, there has been considerable difficulty in applying the standard approaches of classical genetics or even the powerful techniques of molecular biology to the study of opioid receptors. In particular, means are needed for the identification of the DNA sequences encoding individual opioid receptors. Given such isolated, recombinant sequences, it is possible to address the heretofore intractable problems associated with design and testing of isoform-specific opioid receptor agonists and antagonists. The availability of cDNAs encoding the opioid receptors will permit detailed studies of signal-transduction mechanisms and reveal the anatomical distribution of the mRNAs of these receptors, providing information on their expression pattern in the nervous system. This information should ultimately allow better understanding of the opioid system in analgesia, and also the design of more specific therapeutic drugs.

Availability of polynucleotide sequences encoding opioid receptors, and the polypeptide sequences of the encoded receptors, will significantly increase the capability to design pharmaceutical compositions, such as analgesics, with enhanced specificity of function. In general, the availability of these polypeptide sequences will enable efficient screening of candidate compositions. The principle in operation through the screening process is straightforward: natural agonists and antagonists bind to cell-surface receptors and channels to produce physiological effects; certain other molecules bind to receptors and channels; therefore, certain other molecules may produce physiological effects and act as therapeutic pharmaceutical agents. Thus, the ability of candidate drugs to bind to opioid receptors can function as an extremely effective screening criterion for the selection of pharmaceutical compositions with a desired functional efficacy.

Prior methods for screening candidate drug compositions based on their ability to preferentially bind to cell-surface receptors has been limited to tissue-based techniques. In these techniques, animal tissues rich in the receptor type of interest are extracted and prepared; candidate drugs are then allowed to interact with the prepared tissue and those found to bind to the receptors are selected for further study. However, these tissue-based screening techniques suffer from several significant disadvantages. First, they are expensive because the source of receptor cell tissue—laboratory animals—is expensive. Second, extensive technical input is required to operate the screens. And, third, the screens may confuse the results because there are no tissues where only one receptor subtype is expressed exclusively. With traditional prior art screens, the wrong interactions are observed or, at best, the proper interactions are observed together with unwanted interactions.

The nucleic acid molecules, proteins and methods of the subject invention overcome the difficulties discussed supra in connection with kappa$_3$ opioid receptors.

SUMMARY OF THE INVENTION

The subject invention provides recombinant nucleic acid molecule which encodes a kappa$_3$ opioid receptor.

The subject invention further provides an anti-sense oligonucleotide molecule capable of specifically hybridizing to an mRNA molecule encoding kappa$_3$ opioid receptor, at the portion thereof encoding kappa$_3$ opioid receptor, so as to prevent translation of the MRNA molecule.

The subject invention further provides a nucleic acid molecule encoding the anti-sense oligonucleotide molecule of the subject invention, wherein the nucleic acid molecule is capable of being expressed in a suitable host cell.

The subject invention further provides a vector comprising the recombinant nucleic acid molecule of the subject invention.

The subject invention further provides a host vector system for the production of a kappa$_3$ opioid receptor which comprises the vector of the subject invention in a suitable host cell.

The subject invention further provides a method for producing a kappa$_3$ opioid receptor which comprises growing the host vector system of the subject invention under conditions permitting the production of the kappa$_3$ opioid receptor, and recovering the kappa$_3$ opioid receptor produced thereby.

The subject invention further provides the nucleic acid molecule of the subject invention, wherein the nucleic acid molecule is labeled with a detectable marker.

The subject invention further provides al method for detecting the presence of kappa$_3$ opioid receptor-encoding nucleic acid molecules present in a sample which comprises contacting the sample with the labeled nucleic acid molecule of the subject invention under conditions permitting the labeled nucleic acid molecule to form a complex with kappa$_3$ opioid receptor-encoding nucleic acid molecules present in the sample, and detecting the presence of such complex formed so as to thereby detect the presence of kappa$_3$ opioid receptor-encoding nucleic acid molecules present in the sample.

The subject invention further provides a method for quantitatively determining the amount of kappa$_3$ opioid receptor-encoding nucleic acid molecules present in a sample which comprises contacting the sample with a suitable amount of the labeled nucleic acid molecule of the subject invention under conditions permitting the labeled nucleic acid molecule to form a complex with kappa$_3$ opioid receptor-encoding nucleic acid molecules present in the sample, quantitatively determining the amount of complex so formed so as to thereby quantitatively determine the amount of kappa$_3$ opioid receptor-encoding nucleic acid molecules present in the sample.

The subject invention further provides a purified native kappa$_3$ opioid receptor.

The subject invention further provides the variant kappa$_3$ opioid receptor encoded by the recombinant nucleic acid molecule of the subject invention.

The subject invention further provides a method for obtaining partially purified polyclonal antibodies capable of specifically binding to kappa$_3$ opioid receptor and thereby competing with opioid binding thereto which method comprises (a) immunizing a subject with the kappa$_3$ opioid receptor encoded by the nucleic acid molecule of the subject invention, (b) recovering from the immunized subject serum comprising antibodies capable of specifically binding to kappa$_3$ opioid receptor and thereby competing with opioid binding thereto, and (c) partially purifying the antibodies present in the serum, thereby obtaining partially purified polyclonal antibodies capable of specifically binding to kappa$_3$ opioid receptor and thereby competing with opioid binding thereto.

The subject invention further provides the partially purified antibodies produced by the method of the subject invention.

The subject invention further provides a method for obtaining a purified monoclonal antibody capable of specifically binding to kappa$_3$ opioid receptor and thereby competing with opioid binding thereto which method comprises (a) immunizing a subject with the kappa$_3$ opioid receptor encoded by the nucleic acid molecule of the subject invention, (b) recovering from the immunized subject a B cell-containing cell sample, (c) contacting the B cell-containing cell sample so recovered with myeloma cells under conditions permitting fusion of the myeloma cells with the B cells therein so as to form hybridoma cells, (d) isolating from the resulting sample a hybridoma cell capable of producing a monoclonal antibody capable of specifically binding to kappa$_3$ opioid receptor and thereby competing with opioid binding thereto, (e) growing the hybridoma cell so isolated under conditions permitting the production of the monoclonal antibody, and (f) recovering the monoclonal antibody so produced, thereby obtaining a purified monoclonal antibody capable of specifically binding to kappa$_3$ opioid receptor and thereby competing with opioid binding thereto.

The subject invention further provides the hybridoma cell produced in step (d) of the subject invention.

The subject invention further provides the purified monoclonal antibody produced by the method of the subject invention.

The subject invention further provides an antibody capable of specifically binding to kappa$_3$ opioid receptor and thereby competing with opioid binding thereto, said antibody being labeled with a detectable marker.

The subject invention further provides a method for detecting the presence of kappa$_3$ opioid receptor in a sample which comprises contacting the sample with the antibody of the subject invention under conditions permitting the antibody to form a complex with kappa$_3$ opioid receptor present in the sample, and detecting the presence of complex so formed, so as to thereby detect the presence of kappa$_3$ opioid receptor in the sample.

The subject invention further provides a method for quantitatively determining the amount of kappa$_3$ opioid receptor in a sample which comprises contacting the sample with the antibody of the subject invention under conditions permitting the antibody to form a complex with kappa$_3$ opioid receptor present in the sample, quantitatively determining the amount of complex so formed, and comparing the amount so determined with a known standard, so as to thereby quantitatively determine the amount of kappa$_3$ opioid receptor in the sample.

The subject invention further provides a composition which comprises the antibody of the subject invention in an amount effective to permit imaging cell membrane-bound kappa$_3$ opioid receptor present in a subject, and a pharmaceutically acceptable carrier.

The subject invention further provides a method for imaging cell membrane-bound kappa$_3$ opioid receptor present in a subject which comprises administering to the subject an amount of the composition of the subject invention effective to permit imaging cell membrane-bound kappa$_3$ opioid receptor present in the subject under conditions permitting the antibody of the composition to specifically bind to cell membrane-bound kappa$_3$ opioid receptor present in the subject, and imaging the antibody specifically bound to cell membrane-bound kappa$_3$ opioid receptor present in the subject after a suitable period of time, so as to thereby image cell membrane-bound kappa$_3$ opioid receptor present in the subject.

The subject invention further provides a composition which comprises the antibody of the subject invention in an amount effective to permit quantitatively determining the amount of cell membrane-bound kappa$_3$ opioid receptor present in a subject, and a pharmaceutically acceptable carrier.

The subject invention further provides a method for quantitatively determining the amount of cell membrane-bound kappa$_3$ opioid receptor present in a subject which comprises administering to the subject an amount of the composition of the subject invention effective to permit quantitatively determining the amount of cell membrane-bound kappa$_3$ opioid receptor present in the subject under conditions permitting the antibody of the composition to specifically bind to cell membrane-bound kappa$_3$ opioid receptor in the subject, quantitatively determining the amount of antibody specifically bound to cell membrane-associated kappa$_3$ opioid receptors present in the subject, and comparing the amount so determined with a known standard so as to thereby quantitatively determine the amount of cell membrane-bound kappa$_3$ opioid receptor present in the subject.

The subject invention further provides a method for determining a subject's potential sensitivity to a kappa$_3$ opioid receptor-specific agent which comprises quantitatively determining the amount of cell membrane-bound kappa$_3$ opioid receptor present in the subject by the method of the subject invention, and comparing the amount of cell membrane-bound kappa$_3$ opioid receptor so determined with the amount of cell membrane-bound kappa$_3$ opioid receptor present in a subject having a known sensitivity to the agent, so as to thereby determine the subject's potential sensitivity to the kappa$_3$ opioid receptor-specific agent.

The subject invention further provides a method for determining the affinity of an agent for kappa$_3$ opioid receptor which comprises (a) contacting a predetermined amount of kappa$_3$ opioid receptor with (i) a predetermined amount of the agent together with (ii) a predetermined amount of a detectable known ligand of kappa$_3$ opioid receptor, said known ligand being a known ligand of kappa$_3$ opioid receptor with a known affinity therefore, under conditions which would permit the formation of a complex between kappa$_3$ opioid receptor and the detectable known ligand in the absence of the agent, (b) quantitatively determining the amount of kappa$_3$ opioid receptor-detectable known ligand complex so formed, (c) comparing the amount of kappa$_3$ opioid receptor-detectable known ligand complex determined in step (b) with the amount of kappa$_3$ opioid receptor-detectable known ligand complex formed in the absence of the agent, and (d) determining the affinity of the agent for kappa$_3$ opioid receptor based on the comparison in step (c).

The subject invention further provides a, method for determining the affinity of an agent for kappa$_3$ opioid receptor which comprises (a) contacting kappa$_3$ opioid receptor with the agent under conditions which would permit the formation of a complex between kappa$_3$ opioid receptor and a known ligand thereof, (b) contacting a predetermined amount of the agent-receptor complex with a predetermined amount of the antibody of the subject invention under conditions which would permit the formation of a complex between kappa$_3$ opioid receptor and the antibody in the absence of the agent, (c) quantitatively determining the amount of kappa$_3$ opioid receptor-antibody complex so formed, and (d) determining the affinity of the agent for kappa$_3$ opioid receptor based on the amount of kappa$_3$ opioid receptor-antibody complex determined in step (c).

The subject invention further provides a method for determining whether a known ligand of kappa$_3$ opioid receptor is an agonist thereof which comprises (a) contacting the kappa$_3$ opioid receptor with (i) a predetermined amount of the ligand and (ii) a predetermined amount of GTP or analog thereof under conditions which would permit the binding of the ligand to the kappa$_3$ opioid receptor in the absence of GTP or analog thereof, (b) quantitatively determining the percentage of such predetermined amount of ligand bound to the kappa$_3$ opioid receptor, and (c) comparing the percentage so determined with the percentage of such predetermined amount of ligand bound to the kappa$_3$ opioid receptor in the absence of GTP or analog thereof, a lower percentage in the presence of GTP or analog thereof relative to the percentage in the absence of GTP or analog thereof indicating that the ligand is an agonist of kappa$_3$ opioid receptor.

Finally, the subject invention provides a method for determining whether a ligand of kappa$_3$ opioid receptor is an antagonist thereof which comprises (a) contacting the kappa$_3$ opioid receptor with (i) a predetermined amount of the ligand and (ii) a predetermined amount of GTP or analog thereof under conditions which would permit the binding of the ligand to the kappa$_3$ opioid receptor in the absence of GTP or analog thereof, (b) quantitatively determining the percentage of such predetermined amount of ligand bound to the kappa$_3$ opioid receptor, and (c) comparing the percentage so determined with the percentage of such predetermined amount of ligand bound to the kappa$_3$ opioid receptor in the absence of GTP or analog thereof, an equality between the percentage in the presence of GTP or analog thereof and the percentage in the absence of GTP or analog thereof indicating that the ligand is an antagonist of kappa$_3$ opioid receptor.

BRIEF DESCRIPTION OF THE FIGURES

FIGS. 1A–1D Nucleic acid sequence (SEQ. ID NO:1) of mouse kappa$_3$ opioid receptor cDNA and predicted amino acid sequence (SEQ. ID NO:2) thereof.

DETAILED DESCRIPTION OF THE INVENTION

Figure 2:
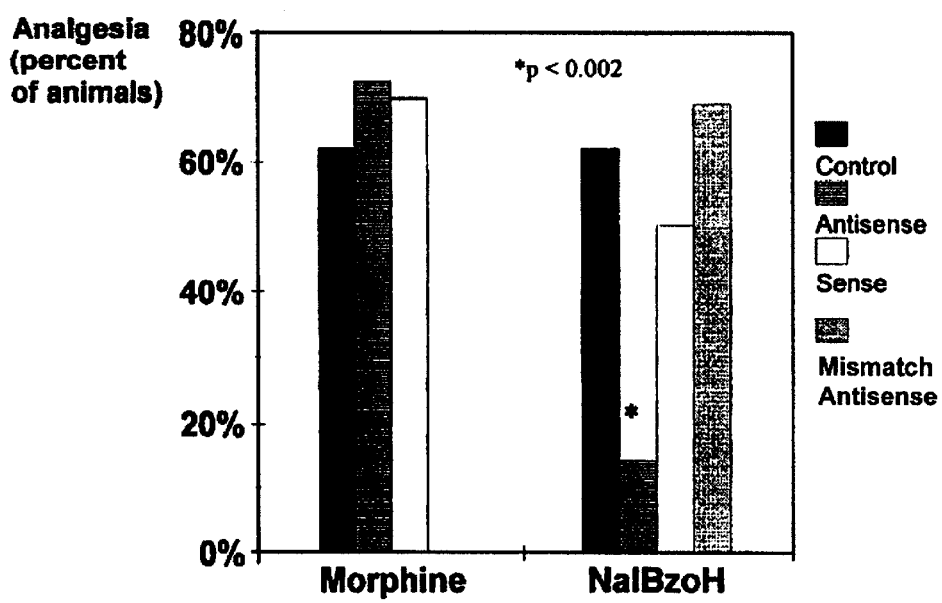
FIG. 2 Effect of antisense treatment on kappa$_3$ analgesic activity.

The plasmid 13-2A4 was deposited pursuant to, and in satisfaction of, the requirements of the Budapest Treaty on the International Recognition of the Deposit of Microorganisms for the Purposes of Patent Procedure with the American Type Culture Collection (ATCC), 10801 University Blvd., Manassas, Va. 20110-2209 under ATCC Accession No. 75608. The plasmid 13-2A4 was deposited with the ATCC on Nov. 5, 1993.

Specifically, the subject invention provides recombinant nucleic acid molecule which encodes a kappa$_3$ opioid receptor.

As used herein, a recombinant nucleic acid molecule is a nucleic acid molecule which does not occur as an individual molecule in nature and which is obtained through the use of recombinant technology.

The designation "kappa$_3$ opioid receptor" includes all opioid receptors which display the pharmacological behavior attributed to kappa$_3$ opioid receptors, including kappa$_3$-like opioid receptors such as the kapppa opioid receptor-3 ("KOR-3").

In one embodiment, the nucleic acid molecule is a DNA molecule. The DNA molecule may be a cDNA molecule. In another embodiment, the nucleic acid molecule is an RNA molecule. The RNA molecule may be an mRNA molecule.

In one embodiment, the kappa$_3$ opioid receptor is native kappa$_3$ opioid receptor. Native kappa$_3$ opioid receptor means a full length, naturally occurring membrane-bound kappa$_3$ opioid receptor protein.

In another embodiment, the kappa$_3$ opioid receptor is a variant kappa$_3$ opioid receptor. As used herein, variant kappa$_3$ opioid receptor means a protein comprising a portion of kappa$_3$ opioid receptor, which protein portion is capable of (a) specifically binding to a kappa$_3$ opioid receptor-specific ligand, and (b) competing with kappa$_3$ opioid receptor for binding to a kappa$_3$ opioid receptor-specific ligand. A variant kappa$_3$ opioid receptor may comprise, by way of example, a fragment of kappa$_3$ opioid receptor, a point mutant of kappa$_3$ opioid receptor, a deletion mutant of kappa$_3$ opioid receptor, or a point and deletion mutant of kappa$_3$ opioid receptor. The variant kappa$_3$ opioid receptor may be an aqueous-soluble variant kappa$_3$ opioid receptor, and may either be glycosylated or non-glycosylated.

The kappa$_3$ opioid receptor may be a mammalian kappa$_3$ opioid receptor. In one embodiment, the mammalian kappa$_3$ opioid receptor is a murine kappa$_3$ opioid receptor. The murine kappa$_3$ opioid receptor may be the murine kappa$_3$ opioid receptor having the sequence shown in FIG. 1. In another embodiment, the mammalian kappa$_3$ opioid receptor is a human kappa$_3$ opioid receptor.

The subject invention further provides an anti-sense oligonucleotide molecule capable of specifically hybridizing to an mRNA molecule encoding kappa$_3$ opioid receptor, at the portion thereof encoding kappa$_3$ opioid receptor, so as to prevent translation of the mRNA molecule. Such anti-sense oligonucleotide molecules are discussed in more detail infra.

As used herein, "capable of specifically hybridizing" means capable of binding to an mRNA molecule encoding kappa$_3$ opioid receptor but not capable of binding to an mRNA molecule encoding a non-kappa$_3$ opioid receptor protein.

The subject invention further provides a nucleic acid molecule encoding the anti-sense oligonucleotide molecule of the subject invention, wherein the nucleic acid molecule is capable of being expressed in a suitable host cell. In one embodiment, the nucleic acid molecule encoding the anti-sense oligonucleotide molecule is a DNA molecule.

The subject invention further provides a vector comprising the recombinant nucleic acid molecule of the subject invention.

In accordance with the invention, numerous vector systems for expression of kappa$_3$ opioid receptor may be employed. For example, one class of vectors utilizes DNA elements which are derived from animal viruses such as bovine papilloma virus, polyoma virus, adenovirus, vaccinia virus, baculovirus, retroviruses (RSV, MMTV or MOMLV), Semliki Forest virus or SV40 virus. Additionally, cells which have stably integrated the DNA into their chromosomes may be selected by introducing one or more markers which allow for the selection of transfected host cells. The marker may provide, for example, prototropy to an auxotrophic host, biocide resistance, (e.g., antibiotics) or resistance to heavy metals such as copper or the like. The selectable marker gene can be either directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals.

In one embodiment, the vector is a plasmid. The plasmid may be the plasmid designated 13-2A4 (ATCC Accession No. 75608.

The subject invention further provides a host vector system for the production of a kappa$_3$ opioid receptor which comprises the vector of the subject invention in a suitable host cell. Methods of making host vector systems are well known to those skilled in the art.

The suitable host cell may be a bacterial cell. In one embodiment, the bacterial cell is an *E. coli* cell.

The suitable host cell may also be an eucaryotic cell. In one embodiment, the eucaryotic cell is a mammalian cell. In the preferred embodiment, the mammalian cell is a COS cell. The COS cell may be a COS-7 cell.

The subject invention further provides a method for producing a kappa$_3$ opioid receptor which comprises growing the host vector system of the subject invention under conditions permitting the production of the kappa$_3$ opioid receptor, and recovering the kappa$_3$ opioid receptor produced thereby.

Methods and conditions for growing host vector systems and for recovering the kappa$_3$ opioid receptor so produced are well known to those skilled in the art, and may be varied or optimized depending upon the specific vector and host cell employed. Such recovery methods include, by way of example, gel electrophoresis, ion exchange chromatography, affinity chromatography or combinations thereof.

The subject invention further provides the nucleic acid molecule of the subject invention, wherein the nucleic acid molecule is labeled with a detectable marker. In one embodiment, the labeled nucleic acid molecule of the subject invention need not encode a functional receptor, but need only possess sufficient homology to a functional kappa$_3$ opioid receptor sequence to permit hybridization thereto.

The subject invention further provides a method for detecting the presence of kappa$_3$ opioid receptor-encoding nucleic acid molecules present in a sample which comprises contacting the sample with the labeled nucleic acid molecule of the subject invention under conditions permitting the labeled nucleic acid molecule to form a complex with kappa$_3$ opioid receptor-encoding nucleic acid molecules present in the sample, and detecting the presence of such complex formed so as to thereby detect the presence of kappa$_3$ opioid receptor-encoding nucleic acid molecules present in the sample.

The nucleic acid molecules detected may be DNA or RNA molecules. In one embodiment, the nucleic acid molecules detected are mRNA molecules.

The sample may be, for example, a solution comprising nucleic acid molecules, or an immobilized sample of nucleic acid molecules.

Conditions permitting the labeled nucleic acid molecule to form a complex with kappa$_3$ opioid receptor-encoding nucleic acid molecules present in the sample, as well as methods for detecting the presence of such complex formed, are well known in the art.

The subject invention further provides a method for quantitatively determining the amount of kappa$_3$ opioid receptor-encoding nucleic acid molecules present in a sample which comprises contacting the sample with a suitable amount of the labeled nucleic acid molecule of the subject invention under conditions permitting the labeled nucleic acid molecule to form a complex with kappa$_3$ opioid receptor-encoding nucleic acid molecules present in the sample, quantitatively determining the amount of complex so formed so as to thereby quantitatively determine the amount of kappa$_3$ opioid receptor-encoding nucleic acid molecules present in the sample.

The amount of kappa$_3$ opioid receptor-encoding nucleic acid molecules present in a sample need not be an absolute number, in the sense that it need not be the actual number of nucleic acid molecules in the sample. Rather, the amount may merely correlate with this number.

The subject invention further provides a purified native kappa$_3$ opioid receptor. As used herein, "purified" means free of any other opioid receptors. For example, the purified kappa$_3$ opioid receptor may include membrane fragments, other non-kappa$_3$ opioid receptor proteins, and a suitable buffer. Alternatively, the purified kappa$_3$ opioid receptor may include only the receptor, or receptor bound by a membrane, and a suitable buffer.

The subject invention further provides the variant kappa$_3$ opioid receptor encoded by the recombinant nucleic acid molecule of the subject invention. In one embodiment, the variant kappa$_3$ opioid receptor is a purified variant kappa$_3$ opioid receptor.

The subject invention further provides a method for obtaining partially purified polyclonal antibodies capable of specifically binding to kappa$_3$ opioid receptor and thereby competing with opioid binding thereto.which method comprises (a) immunizing a subject with the kappa$_3$ opioid receptor encoded by the nucleic acid molecule of the subject invention, (b) recovering from the immunized subject serum comprising antibodies capable of specifically binding to kappa$_3$ opioid receptor and thereby competing with opioid binding thereto, and (c) partially purifying the antibodies present in the serum, thereby obtaining partially purified polyclonal antibodies capable of specifically binding to kappa$_3$ opioid receptor and thereby competing with opioid binding thereto.

As used herein, partially purified antibodies means a composition which comprises antibodies which specifically bind to kappa$_3$ opioid receptor, and consists of fewer protein impurities than does the serum from which the antibodies are derived. A protein impurity means a protein other than the antibodies specific for kappa$_3$ opioid receptor. For example, the partially purified antibodies might be an IgG preparation.

Methods of recovering serum from a subject are well known to those skilled in the art. Methods of partially purifying antibodies are also well known to those skilled in the art, and include, by way of example, filtration, ion exchange chromatography, and precipitation.

As used herein, "capable of specifically binding to kappa$_3$ opioid receptor and thereby competing with opioid binding thereto" means binding either directly to an opioid-binding site or to a non-opioid-binding site resulting in inhibition of opioid binding to the receptor.

The subject invention further provides the partially purified antibodies produced by the method of the subject invention.

The subject invention further provides a method for obtaining a purified monoclonal antibody capable of specifically binding to kappa$_3$ opioid receptor and thereby competing with opioid binding thereto which method comprises (a) immunizing a subject with the kappa$_3$ opioid receptor encoded by the nucleic acid molecule of the subject invention, (b) recovering from the immunized subject a B cell-containing cell sample, (c) contacting the B cell-containing cell sample so recovered with myeloma cells under conditions permitting fusion of the myeloma cells with the B cells therein so as to form hybridoma cells, (d) isolating from the resulting sample a hybridoma cell capable of producing a monoclonal antibody capable of specifically binding to kappa$_3$ opioid receptor and thereby competing with opioid binding thereto, (e) growing the hybridoma cell so isolated under conditions permitting the production of the monoclonal antibody, and (f) recovering the monoclonal antibody so produced, thereby obtaining a purified monoclonal antibody capable of specifically binding to kappa$_3$ opioid receptor and thereby competing with opioid binding thereto.

Methods of making hybridomas and monoclonal antibodies are well known to those skilled in the art.

The subject invention further provides the hybridoma cell produced in step (d) of the subject invention.

The subject invention further provides the purified monoclonal antibody produced by the method of the subject invention.

As used herein, a "purified monoclonal antibody" means the monoclonal antibody free of any other antibodies.

The subject invention further provides an antibody capable of specifically binding to kappa$_3$ opioid receptor and thereby competing with opioid binding thereto, said antibody being labeled with a detectable marker.

The labeled antibody may be a polyclonal or monoclonal antibody. In one embodiment, the labeled antibody is a purified labeled antibody. The term "antibody" includes, by way of example, both naturally occurring and non-naturally occurring antibodies. Specifically, the term "antibody" includes polyclonal and monoclonal antibodies, and fragments thereof. Furthermore, the term "antibody" includes chimeric antibodies and wholly synthetic antibodies, and fragments thereof. The detectable marker may be, for example, radioactive or fluorescent. Methods of labeling antibodies are well known in the art.

The subject invention further provides a method for detecting the presence of kappa$_3$ opioid receptor in a sample which comprises contacting the sample with the antibody of the subject invention under conditions permitting the antibody to form a complex with kappa$_3$ opioid receptor present in the sample, and detecting the presence of complex so formed, so as to thereby detect the presence of kappa$_3$ opioid receptor in the sample.

The sample may be, for example, a cell sample, tissue sample, or protein-containing fluid sample. Conditions permitting the antibody to form a complex with kappa$_3$ opioid receptor and methods of detecting the presence of complex so formed are well known in the art.

The subject invention further provides a method for quantitatively determining the amount of kappa$_3$ opioid receptor in a sample which comprises contacting the sample with the antibody of the subject invention under conditions permitting the antibody to form a complex with kappa$_3$ opioid receptor present in the sample, quantitatively determining the amount of complex so formed, and comparing the amount so determined with a known standard, so as to thereby quantitatively determine the amount of kappa$_3$ opioid receptor in the sample.

The subject invention further provides a composition which comprises the antibody of the subject invention in an amount effective to permit imaging cell membrane-bound kappa$_3$ opioid receptor present in a subject, and a pharmaceutically acceptable carrier.

The amount effective to permit imaging cell membrane-bound kappa$_3$ opioid receptor present in a subject may be calculated using methods well known in the art.

Pharmaceutically acceptable carriers are well known to those skilled in the art and include, but are not limited to, 0.01–0.1M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

The subject invention further provides a method for imaging cell membrane-bound $kappa_3$ opioid receptor present in a subject which comprises administering to the subject an amount of the composition of the subject invention effective to permit imaging cell membrane-bound $kappa_3$ opioid receptor present in the subject under conditions permitting the antibody of the composition to specifically bind to cell membrane-bound $kappa_3$ opioid receptor present in the subject, and imaging the antibody specifically bound to cell membrane-bound $kappa_3$ opioid receptor present in the subject after a suitable period of time, so as to thereby image cell membrane-bound $kappa_3$ opioid receptor present in the subject.

In one embodiment, the subject is a mouse. In another embodiment, the subject is a human.

As used herein, "imaging" means determining the physical location of cell membrane-bound $kappa_3$ opioid receptor present in the subject. General methods of imaging cell membrane-bound proteins using antibody-based probes are well known to those skilled in the art. The signal detected in the imaging method of the subject invention consists of signal from labeled antibody bound to cell membrane-bound $kappa_3$ opioid receptor. The amount of antibody may be saturating or non-saturating. As used herein, "saturating" means that the number of receptor binding-sites on the antibodies exceeds the number of antibody-binding sites on the receptors.

Imaging the antibody specifically bound to cell membrane-bound $kappa_3$ opioid receptor is accomplished according to methods well known to those skilled in the art. Such methods include, by way of example, using a gamma camera to measure the signal emitted by the antibody bound to receptor present in a subject. The imaging methods and quantitative methods of the subject invention can be combined, and means of doing so are well known in the art.

As used herein, a "suitable period of time" means a period of time after which substantially all of the non-specifically bound antibody has be excreted from the subject, but by which a detectable amount of antibody remains bound to the receptor present in the subject.

The subject invention further provides a composition which comprises the antibody of the subject invention in an amount effective to permit quantitatively determining the amount of cell membrane-bound $kappa_3$ opioid receptor present in a subject, and a pharmaceutically acceptable carrier.

The amount effective to permit quantitatively determining the amount of cell membrane-bound $kappa_3$ opioid receptor can be determined according to methods well known in the art.

The subject invention further provides a method for quantitatively determining the amount of cell membrane-bound $kappa_3$ opioid receptor present in a subject which comprises administering to the subject an amount of the composition of the subject invention effective to permit quantitatively determining the amount of cell membrane-bound $kappa_3$ opioid receptor present in the subject under conditions permitting the antibody of the composition to specifically bind to cell membrane-bound $kappa_3$ opioid receptor in the subject, quantitatively determining the amount of antibody specifically bound to cell membrane-associated $kappa_3$ opioid receptors present in the subject, and comparing the amount so determined with a known standard so as to thereby quantitatively determine the amount of cell membrane-bound $kappa_3$ opioid receptor present in the subject.

The amount of the composition effective to permit quantitatively determining the amount of receptor, conditions permitting the antibody to specifically bind to $kappa_3$ opioid receptor, and methods of quantitatively determining the amount of antibody specifically bound to the receptors are well known in the art.

The amount of cell membrane-bound $kappa_3$ opioid receptor need not be an absolute number, in the sense that it need not be the actual number of receptors in the subject. Rather, the amount may merely correlate with this number.

The methods of the subject invention for imaging and quantitatively determining the amount of receptor in an entire subject may be analogously applied to individual organs in the subject.

The subject invention further provides a method for determining a subject's potential sensitivity to a $kappa_3$ opioid receptor-specific agent which comprises quantitatively determining the amount of cell membrane-bound $kappa_3$ opioid receptor present in the subject by the method of the subject invention, and comparing the amount of cell membrane-bound $kappa_3$ opioid receptor so determined with the amount of cell membrane-bound $kappa_3$ opioid receptor present in a subject having a known sensitivity to the agent, so as to thereby determine the subject's potential sensitivity to the $kappa_3$ opioid receptor-specific agent.

As used herein, a subject's potential sensitivity to a $kappa_3$ opioid receptor-specific agent is the degree to which the agent is capable of eliciting a $kappa_3$ opioid receptor-mediated physiological response in the subject.

As used herein, the term "agent" includes both protein and non-protein moieties. For example, the agent may be an antibody directed against a portion of $kappa_3$ opioid receptor, or a $kappa_3$ opioid or analog thereof.

In one embodiment, the $kappa_3$ opioid receptor-specific agent is a $kappa_3$ opioid receptor-specific analgesic agent.

The subject invention further provides a method for determining the affinity of an agent for $kappa_3$ opioid receptor which comprises (a) contacting a predetermined amount of $kappa_3$ opioid receptor with (i) a predetermined amount of the agent together with (ii) a predetermined amount of a detectable known ligand of $kappa_3$ opioid receptor, said known ligand being a known ligand of $kappa_3$ opioid receptor with a known affinity therefore, under conditions which would permit the formation of a complex between $kappa_3$ opioid receptor and the detectable known ligand in the absence of the agent, (b) quantitatively determining the amount of $kappa_3$ opioid receptor-detectable known ligand complex so formed, (c) comparing the amount of $kappa_3$ opioid receptor-detectable known ligand complex determined in step (b) with the amount of $kappa_3$ opioid receptor-detectable known ligand complex formed in the absence of the agent, and (d) determining the affinity of the agent for kappa$_3$ opioid receptor based on the comparison in step (c).

The detectable known ligand of kappa$_3$ opioid receptor may be, for example, radiolabeled, fluorescently labeled or enzymatically labeled.

Conditions permitting the formation of a complex, and methods for quantitatively determining the amount of receptor-ligand complex are well known in the art. Methods of determining the affinity of the agent for kappa$_3$ opioid receptor based on the comparison in step (c) are also well known in the art.

The subject invention further provides a method for determining the affinity of an agent for kappa$_3$ opioid receptor which comprises (a) contacting kappa$_3$ opioid receptor with the agent under conditions which would permit the formation of a complex between kappa$_3$ opioid receptor and a known ligand thereof, (b) contacting a predetermined amount of the agent-receptor complex with a predetermined amount of the antibody of the subject invention under conditions which would permit the formation of a complex between kappa$_3$ opioid receptor and the antibody in the absence of the agent, (c) quantitatively determining the amount of kappa$_3$ opioid receptor-antibody complex so formed, and (d) determining the affinity of the agent for kappa$_3$ opioid receptor based on the amount of kappa$_3$ opioid receptor-antibody complex determined in step (c).

The subject invention further provides a method for determining whether a known ligand of kappa$_3$ opioid receptor is an agonist thereof which comprises (a) contacting the kappa$_3$ opioid receptor with (i) a predetermined amount of the ligand and (ii) a predetermined amount of GTP or analog thereof under conditions which would permit the binding of the ligand to the kappa$_3$ opioid receptor in the absence of GTP or analog thereof, (b) quantitatively determining the percentage of such predetermined amount of ligand bound to the kappa$_3$ opioid receptor, and (c) comparing the percentage so determined with the percentage of such predetermined amount of ligand bound to the kappa$_3$ opioid receptor in the absence of GTP or analog thereof, a lower percentage in the presence of GTP or analog thereof relative to the percentage in the absence of GTP or analog thereof indicating that the ligand is an agonisft of kappa$_3$ opioid receptor.

The conditions, and methods of comparing, in this method are well known in the art. GTP analogs include, by way of example, Gpp(NH$_2$)p and gamma-S-GTP.

The subject invention further provides a method for determining whether a known ligand of kappa$_3$ opioid receptor is an agonist thereof which comprises (a) contacting the kappa$_3$ opioid receptor with a predetermined amount of the ligand under conditions which permit the binding of the ligand to the kappa$_3$ opioid receptor, (b) quantitatively determining the percentage of such predetermined amount of ligand bound to the kappa$_3$ opioid receptor, and (c) comparing the percentage to a known standard so as to thereby determine whether the known ligand of kappa$_3$ opioid receptor is an agonist thereof.

The subject invention further provides a method for determining whether a ligand of kappa$_3$ opioid receptor is an antagonist thereof which comprises (a) contacting the kappa$_3$ opioid receptor with (i) a predetermined amount of the ligand and (ii) a predetermined amount of GTP or analog thereof under conditions which would permit the binding of the ligand to the kappa$_3$ opioid receptor in the absence of GTP or analog thereof, (b) quantitatively determining the percentage of such predetermined amount of ligand bound to the kappa$_3$ opioid receptor, and (c) comparing the percentage so determined with the percentage of such predetermined amount of ligand bound to the kappa$_3$ opioid receptor in the absence of GTP or analog thereof, an equality between the percentage in the presence of GTP or analog thereof and the percentage in the absence of GTP or analog thereof indicating that the ligand is an antagonist of kappa$_3$ opioid receptor.

The subject invention further provides a method for determining whether a known ligand of kappa$_3$ opioid receptor is an antagonist thereof which comprises (a) contacting the kappa$_3$ opioid receptor with a predetermined amount of the ligand under conditions which permit the binding of the ligand to, the kappa$_3$ opioid receptor, (b) quantitatively determining the percentage of such predetermined amount of ligand bound to the kappa$_3$ opioid receptor, and (c) comparing the percentage to a known standard so as to thereby determine whether the known ligand of kappa$_3$ opioid receptor is an antagonist thereof.

Finally, the subject invention provides kits for practicing the methods of the subject invention.

In order to facilitate an understanding of the Experimental Details section which follows, certain frequently occurring methods and/or terms are best described in Sambrook, et al. (1989).

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

I—Introduction

Opiate receptors mediate the actions of the opiates and opioid peptides. For many years, it has been known that a variety of opioid receptor subtypes exist. The first class of opiate receptors identified were termed mu and were based upon the selectivity of drugs such as morphine. This classification was soon followed by additional binding sites called delta receptors, based upon enkephalin binding, and then kappa receptors, which are thought to mediate the actions of dynorphins. Recently multiple subtypes of kappa receptors have been proposed (see, e.g., Pasternak, Clin. Neuropharmacol., 1993, for review and references). The kappa, receptor was initially defined in binding studies using drugs such as U50,488H and nor-binaltorphimine (norBNI). The kappa$_2$ receptor differs from the kappa$_1$ receptor in terms of the binding selectivity. Another kappa receptor subtype was identified which subtype is unique. Like the kappa$_2$ receptor, the kappa$_3$ receptors (Clark, et al. (1989), Price, et al. (1988), Gistrak, et al. (1989), and Paul, et al. (1989)) do not bind U50,488H or nor-binaltorphimine very well. The overall binding selectivity of kappa$_3$ is quite different from that of the kappa$_2$ receptor as well as that of any other published receptor class. In addition to the unique binding profile, the kappa$_3$ receptors have a novel and distinctive pharmacology. Using a novel ligand, naloxone benzoylhydrazone (NalBzoH), the ability of kappa$_3$ receptors to elicit analgesia was confirmed. This kappa$_3$ analgesia does not appear to be associated with respiratory depression or significant constipation. In this regard, the kappa$_3$ analgesia is quite distinct from the actions of morphine. Furthermore, antagonists which selectively block morphine (mu), delta and kappa, analagesia have little effect on kappa$_3$ analgesia. This observation is consistent with a unique site of action. Finally, the continued administration of an opiate drug produces tolerance, i.e., a diminishing response to a repeated fixed dose of drug. Tolerance is seen with virtually all the opioid receptor classes. However, there is no cross-tolerance between kappa$_3$ receptors and the receptors of the other classes. This absence of cross-tolerance implies that the mechanisms of both analgesia and tolerance associated with the kappa$_3$ receptor are distinct from the mechanisms of mu, delta and kappa$_1$ receptors. Based upon these observations, kappa$_3$ receptors represent a novel and unique class of opioid receptor. However, validation of this concept requires the isolation and structural determination of the receptor, a membrane-bound protein. Described herein is the isolation of a cDNA clone encoding for a novel protein which appears to be the kappa$_3$ receptor.

II—Cloning and Sequencing Strategy for Kappa$_3$ Opioid Receptor

Two degenerate oligonucleotides were designed to encode the predicted peptide sequences of the mouse δ receptor at peptide position 137-144 (sense orientation) and 312-319 (anti-sense orientation), which are highly conserved among the G protein-coupled receptor family. The oligonucleotides were used in PCR reactions to amplify mouse kappa$_3$ opioid receptor cDNA from a mouse brain lambda ZAP cDNA library (Stratagene). The PCR amplification resulted in the production of an approximately 500 bp fragment which was subcloned into the Bluescript SK(−) at the EcoRV site. The DNA sequences of the fragment were determined. The nucleotide and predicted peptide sequences of the PCR fragment were highly homologous with those of the mouse δ receptor.

The PCR fragment was radiolabeled with α[32P]dCTP and used as a probe to screen the same mouse brain lambda ZAP cDNA library by hybridization. Approximately 2.8× $10^6$ plaques were probed at high stringency. Eighteen clones were isolated from this screening. The Bluescript SK(−) plasmids containing inserts were then excised from these clones with super-infection of VCSM 13 helper bacteriophage and sizes were verified. One of the longest clones (13-2A4) contains an insert of approximately 2.6 kb. The entire clone was sequenced. The protein sequence is predicted to begin at the first ATG at nucleotide number 96 in the sequence, preceded by two termination codons upstream at positions 7 and 72.

The amino acid sequence predicted from the cDNA encodes a protein containing 367 residues with a calculated molecular weight of 41,047 daltons, and reveals seven hydrophobic domains.

Comparison of the protein sequence with published structures from the opioid receptor family indicates an overall identity with MOR-1, KOR-1 and DOR-1 predicted protein sequences of 50.1%, 48% and 46%, respectively. However, these homology values are somewhat misleading. Portions of the molecule, especially the N- and C-termini, are relatively unique, sharing little homology with the other cloned receptors. However, some of the transmembrane regions show a very close homology, with stretches of identity exceeding 20 amino acid residues in length at points.

III—Expression of Kappa$_3$ Opioid Receptor

The kappa$_3$ opioid receptor clone was expressed in COS-7 cells (Table 1).

TABLE 1

Expression of opioid binding in COS-7 cells with kappa$_3$ opioid receptor

|  | 3H-Diprenorphine Binding (cpm) |
|---|---|
| pSRα | 789 ± 79 |
| Control | 157 ± 20 |

The XhoI/BamHI fragment of the clone was subcloned into a pSRα expression vector at the XhoI/BamHI sites. COS-7 cells were transfected with 30 μg of plasmid DNA/150 mm plate using DEAE-dextran. The transfected cells were grown at 37° C. for 72 hours and the membranes were harvested for binding assays. Control binding was determined using COS-7 cells which were treated with DEAE-dextran and incubated under the same conditions as the transfected cells. $^3$H-Diprenorphine binding was determined in samples with 0.5 mg protein/tube. All binding was assayed in triplicate, except for nonspecific binding in the pSRα which was assayed in duplicate. Only specific opioid binding (i.e., total minus nonspecific) is presented. Results are the means±s.e.m. The pSRα results are significantly different from the control COS-7 cells ($p<0.001$) as determined by the t-Test.

The XhoI/BamHI fragment of the clone was obtained and subcloned into a pSRα expression vector at the XhoI/BamHI sites and then transfected the COS-7 cells, which were assayed for opioid binding after 72 hours. To control for the treatments, the binding in COS-7 cells was also examined, which cells were exposed to DEAE-dextran and incubated under the same conditions as the transfected cells. Additional studies using pCMV vectors and the same transfection techniques reveal binding values virtually identical to those seen in this control (data not shown). Opioid binding was determined with the antagonist $^3$H-diprenorphine. Binding is performed in the absence of a high concentration of active opioid (levallorphan) and specific binding defined as the difference in binding (i.e., the binding sensitive to the active opioid). $^3$H-diprenorphine binding was observed following transfection with the clone which is significantly different from the control binding.

IV—Association of Kappa$_3$ Opioid Receptor in Kappa$_3$ Analgesia

To determine the pharmacological relevance of the clone, an antisense oligodeoxynucleotide was designed and injected intracerebroventricularly in mice as described in section V, infra. Controls consisted of saline vehicle, the complimentary sense oligodeoxynucleotide against the antisense oligodeoxynucleotide and a mismatch antisense oligodeoxynucleotide in which were switched two base pairs from the antisense sequence. As shown in FIG. 2, the antisense treatment markedly lowered the analgesic response to NalBzoH ($p<0.002$) without interfering with the response to morphine. The selectivity of the response was confirmed by the lack of activity of the sense strand or the mismatched antisense probe.

V—Effect of Antisense Treatment on Kappa$_3$ Analgesic Activity

Groups of mice received intracerebroventricular injections of 5 μg of either 1) anti-sense to the kappa$_3$ clone (5'-GGGCTGTGCAGAAGCGCAGA-3')(SEQ ID NO:3)

(n=29 in the morphine group and n=29 in the NalBzoH group); 2) the complementary sense strand to this oligodeoxynucleotide (5'-CCCGACACGTCTTCGC-GTCT-3') (SEQ ID NO:4) (n=29 in the morphine group and n=29 in the NalBzoH group); or a mismatch antisense or saline on days 1, 3 and 5. On day 6, animals were tested for analgesia to either morphine (1 μg) or NalBzoH (15 μg). An additional group was treated identically with a mismatched antisense in which two base pairs had been switched (5'-GGGTCGTGCAGAGACGCAGA-3') (SEQ ID NO:5) (n=29) and tested only with NalBzoH. Analgesia was assessed quantally using the tailflick assay. In brief, a mouse tail is exposed to a hot beam of light and the duration of time the mouse permits the tail to remain in the beam of light is measured. Typical latencies range between 2 to 3 seconds. Fifteen minutes after the injection of drug, the test is repeated. Analgesia is defined quantally as a doubling or greater of the tailflick latency compared to the baseline determined for each individual mouse. Statistical significance is determined using the Fischer exact test. Morphine analgesia is unaffected by anti-sense treatment. NalBzoH analgesia is unaffected by the sense or the mismatched antisense treatments, but is markedly reduced by the anti-sense treatment ($p<0.002$).

VI—Conclusion

A clone was isolated and sequenced which appears to correspond to the $kappa_3$ receptor initially proposed several years ago. The clone was expressed in COS-7 cells, as demonstrated by the appearance of opioid binding, indicating that the protein was synthesized. Finally, a highly specific antisense approach was utilized to demonstrate the involvement of the protein encoded by this clone in $kappa_3$ analgesia, but not that of morphine induced analgesia.

References

Adelman et al. (1983) DNA 2:183.
Akil, H. et al. (1984) Annu. Rev. Neurosci. 7:223.
Attali, B. et al. (1989) J. Neurochem. 52:360.
Bertin, B. et al. (1992) J. Biol. Chem. 267(12):8200.
Bero, et al. (1988) Mol;. Pharmacol. 34:614.
Bertolucci, M. et al. Neurosci, Abstr. 18L1368.
Bolivar et al., (1977) Gene, 2:95.
Boshart et al. (1985) Cell 41:521.
Bouvier, M. et al. (1988) Mol. Pharmacol. 33:133.
Bradbury, A. F. et al. (1976) Nature 260:165.
Breder, C. D. et al. (1992). J. Neurosci 12:3920.
Chang et al., (1978) Nature, 375:615.
Clark, J. A. et al. (1989) J. Pharmacol. Expt. Therapeut. 251:461.
Cotecchia et al. (1988) Proc. Natl. Acad. Sci. USA 85:7159.
Crea et al., (1978) Proc. Natl. Acad. Sci. U.S.A, 75:5765.
Danboldt, N. C. et al. (1990) Biochemistry 29(28)-6734.
Di Chiara, G. et al. (1992) Trends Pharmacoll. Sci. 13:185.
Dohlman (1987) Biochemistry 26:2657.
Dohlman, H.G. (1991) Annu. Rev. Biochem. 60:166–170; 174–653–688.
Ferruti, P. and Tanzi, M. C., (1986) Cris. Rev. Ther. Drug Carrier Syst. 2:117–136.
Fiers et al., (1978) Nature 273:113.
Frielle, T. et al. (1988) Proc. Natl. Acad. Sci. USA 85:9484.
Gabizon, A. et al., (1990) Cancer Res. 50:6371–6378
Gioannini, T. L. et al. (1989) J. Mol. Recogn. 2:44.
Goeddel et al., (1979) Nature, 281:544.
Goeddel et al., (1980) Nucleic Acids Res., 8:4057.
Gransch, C. et al. (1988) J. Biol. Chem. 263:5853.
Hess et al., (1968) J. Adv. Enzyme Reg. 7:149.
Hitzeman et al., (1980) J. Biol. Chem. 255:2073.
Holland et al., (1978) Biochemistry 17:4900.
Horstman, D. A. et al. (1990) J. Biol. Chem. 265:21590.
Hsia, J. A. et al. (1984) J. Biol. Chem. 259:1086.
Hughes, J. et al. (1975) Nature 258:577.
Itakura et al., (1977) Science, 198:1056.
Jones, (1977) Genetics 85:12.
Kanaho et al. (1984) J. Biol. Chem. 259:7378.
Kennelly, P. J. et al. (1991) J. Biol. Chem. 266:15555.
King et al. (1990) Science 250:121.
Kingsman et al., (1979) Gene 7:141.
Kobilka, B. K. et al. (1987) J. Biol. Chem. 262:7321.
Kobilka, B. K. et al. (1988) Science 240:1310.
Koob, G. F. et al. (1992) Trends Neurosci. 15:186.
Kozasa et al. (1988) Proc. Natl. Acad. Sci USA 85:2081.
Kruse and Patterson, eds. (1973) Tissue Culture, Academic Press.
Kyte, J., and R. F. Doolittle (1982) J. Mol. Biol. 157:105.
Loh, H. H. et al., (1990) Annu. Rev. Pharmacol. Toxicol. 30:123.
Loh, H. H. et al. (1990) Annu. Rev. Pharmacol. Toxicol. 30:123.
Lomasney et al. (1990) Proc. Natl. Acad. Sci. USA 87:5094.
Lutz, R. A. et al. (1992) J. Receptor Res. 12:267.
Mansour, A. et al. (1987) J. Neurosci. 7:2445.
Marullo et al. (1988) Proc. Natl. Acad. Sci. USA 85:7551.
Messing et al., Third Cleveland Symposium on Macromolecules and Recombinant DNA, Editor A. Walton, Elsevier, Amsterdam (1981).
Nathans et al. (1986 A) Science 232:193.
Nathans et al. (1986 B) Science 232:203
Nock, B. et al. (1988) Eur. J. Pharmacol. 154:27.
Okayama et al. (1983) Mol. Cell Biol. 3:280.
Olson, G. A. et al. (1989) Peptides 10:1253.
Ott, S. et al. (1988) J. Biol. Chem. 263:10524.
Payette et al. (1990) FEBS Lett. 266:21.
Pert, C. G. et al. (1973) Science 179:1011.
Pert, C. B. et al. (1974) Mol. Pharmacol. 10:868.
Pfeiffer, A. et al. (1986) Science 223:774.
Puttfarcken, P. S. et al. (1988) Mol. Pharmacol. 33:520.
Ranade, V. V. (1989) J. Clin. Pharmacol. 29:685–694
Regan et al. (1988) Proc. Natl. Acad. Sci. USA 85:6301.
Sambrook, J. et al. (1989) Molecular Cloning: A Laboratory Manual (Cold Spring Harbor Laboratory Press, Cold Spring Harbor, N.Y.).
Seeburg (1982) DNA 1:239.
Shook, J. E. et al. (1990) Am. Rev. Respir. Dis. 142:895.
Siebwenlist et al., (1980) Cell, 20:269.
Simon, E. J. (1991) Medicinal Res. Rev. 11:357.
Stinchcomb et al., (1979) Nature, 282:39.
Stratford-Perricaudet et al. (1992).
Strotchman and Simon (1991).
Thomsen et al. (1984) PNAS 81:659.
Tschemper et al., (1980) Gene 10:157.
Unterwald, E. M. et al. (1991) Brain Res. 562:57.
Unterwald, E. M. et al. (1987) Eur. J. Pharmacol. 133:275.
Xie, G-X., et al. (1992) Proc. Natl. Acad. Sci. USA 89:4124.
Yamada, Y. et al. (1992) Proc. Natl. Acad. Sci. USA 89:251.
Yasuda, K. et al. (1992) J. Biol Chem. 267:20422.
Yokota, Y. et al. (1992) EMBO J. 11:3585.
Zukin, R. S. et al. (1988) Proc. Natl. Acad. Sci. USA 85:4061.

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 2600 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: N (iv) ANTI-SENSE: N (ix) FEATURE:
      (A) NAME/KEY: CDS
      (B) LOCATION: 299..1401
      (D) OTHER INFORMATION:

(xi) SEQUENCE DESCRIPTION: SEQ ID NO:1:

```
TTTGGCTTCC TTCTCCAACC TGCGCAGCCC CTCCTTCTCT CAGCCGCAGC CTTCTGCCCC      60

TCCCCCTTCT GGCTGCCGCA CTGGCTGCTG CGTCTAGTCA ATATCTTATC TTCGGAGCAG     120

GAGCTAGGAG CCATTCCCAG CCGGAGCAGA CCCCAAGCTA GAGTGAGAAG CATTACTCAG     180

TTCATTGTGC TCCTGCCTGC CTTTCTGCTA AGCATTAGGG TCTGTTTTGG CCCAGCTTCT     240

GAAGAGGTTG TGTGTGCTGT TGGAGGAACT GTACTGAGTG GCTTTGCAGG GTGACAGC      298

ATG GAG TCC CTC TTT CCT GCC CCA TTC TGG GAG GTC TTG TAT GGC AGC      346
Met Glu Ser Leu Phe Pro Ala Pro Phe Trp Glu Val Leu Tyr Gly Ser
  1               5                  10                  15

CAC TTT CAA GGG AAC CTG TCT CTC CTA AAT GAG ACC GTA CCC CAT CAC      394
His Phe Gln Gly Asn Leu Ser Leu Leu Asn Glu Thr Val Pro His His
             20                  25                  30

CTG CTC CTC AAT GCT AGC CAC AGT GCC TTC CTG CCC CTT GGA CTC AAG      442
Leu Leu Leu Asn Ala Ser His Ser Ala Phe Leu Pro Leu Gly Leu Lys
         35                  40                  45

GTC ACC ATC GTG GGG CTC TAC TTG GCT GTG TGC ATC GGG GGG CTC CTG      490
Val Thr Ile Val Gly Leu Tyr Leu Ala Val Cys Ile Gly Gly Leu Leu
     50                  55                  60

GGG AAC TGC CTC GTC ATG TAT GTC ATC CTC AGG CAC ACC AAG ATG AAG      538
Gly Asn Cys Leu Val Met Tyr Val Ile Leu Arg His Thr Lys Met Lys
 65                  70                  75                  80

ACT GCT ACC AAC ATT TAC ATA TTT AAT CTG GCA CTG GCT GAT ACC CTG      586
Thr Ala Thr Asn Ile Tyr Ile Phe Asn Leu Ala Leu Ala Asp Thr Leu
                 85                  90                  95

GTC TTG CTG ACA CTG CCC TTC CAG GGC ACA GAC ATC CTT CTG GGC TTC      634
Val Leu Leu Thr Leu Pro Phe Gln Gly Thr Asp Ile Leu Leu Gly Phe
            100                 105                 110

TGG CCA TTT GGG AAT GCA CTG TGC AAG ACG GTC ATT GCT ATC GAC TAC      682
Trp Pro Phe Gly Asn Ala Leu Cys Lys Thr Val Ile Ala Ile Asp Tyr
        115                 120                 125

TAC AAC ATG TTT ACC AGC ACT TTC ACT TTG ACT GCC ATG AGT GTA GAC      730
Tyr Asn Met Phe Thr Ser Thr Phe Thr Leu Thr Ala Met Ser Val Asp
    130                 135                 140

CGT TAT GTA GCT ATC TGC CAC CCT ATC CGT GCC CTT GAT GTT CGG ACA      778
Arg Tyr Val Ala Ile Cys His Pro Ile Arg Ala Leu Asp Val Arg Thr
145                 150                 155                 160
```

```
TCC AGT AAA GCC CAG GCC GTT AAT GTG GCC ATA TGG GCC TGG CTT CGG     826
Ser Ser Lys Ala Gln Ala Val Asn Val Ala Ile Trp Ala Trp Leu Arg
            165                 170                 175

TGG TTG GTG TTC CTG TTG CCA TCA TGG GCT CAG CAC AAG TGG AGG ATG     874
Trp Leu Val Phe Leu Leu Pro Ser Trp Ala Gln His Lys Trp Arg Met
        180                 185                 190

AAG AGA TCG AGT GCC TGG TGG AGA TCC CCG CCC CTC AGG ACT ATT GGG     922
Lys Arg Ser Ser Ala Trp Trp Arg Ser Pro Pro Leu Arg Thr Ile Gly
            195                 200                 205

GCC CTG TAT TTG CCA TCT GCA TCT TCC TTT TTT CCT TCA TCA TCC CGG     970
Ala Leu Tyr Leu Pro Ser Ala Ser Ser Phe Phe Pro Ser Ser Ser Arg
        210                 215                 220

TTA CTG ATC ATC TCT GTC TGC TAC AGC CTC ATG ATT CGA CGA CTT CGT    1018
Leu Leu Ile Ile Ser Val Cys Tyr Ser Leu Met Ile Arg Arg Leu Arg
225                 230                 235                 240

GGT GTC CGG CTG CTT TCA GGC TCC CGA GAG AAG GAC CGG AAC CTG CGA    1066
Gly Val Arg Leu Leu Ser Gly Ser Arg Glu Lys Asp Arg Asn Leu Arg
            245                 250                 255

CGC ATC ACA CGG CTG GTA CTG GTA GTT GTG GCT GTG TTT GTG GGC TGC    1114
Arg Ile Thr Arg Leu Val Leu Val Val Val Ala Val Phe Val Gly Cys
        260                 265                 270

TGG ACA CCT GTG CAG GTC TTT GTC CTG GTT CAA GGA CTG GGT GTT CAG    1162
Trp Thr Pro Val Gln Val Phe Val Leu Val Gln Gly Leu Gly Val Gln
        275                 280                 285

CCA GGT AGT GAG ACT GCA GTA GCC ATT CTG CGC TTC TGC ACA GCC CTG    1210
Pro Gly Ser Glu Thr Ala Val Ala Ile Leu Arg Phe Cys Thr Ala Leu
        290                 295                 300

GGC TAT GTC AAC AGT TGT CTC AAT CCC ATT CTC TAT GCT TTC TTG GAT    1258
Gly Tyr Val Asn Ser Cys Leu Asn Pro Ile Leu Tyr Ala Phe Leu Asp
305                 310                 315                 320

GAG AAC TTC AAG GCC TGC TTT AGA AAG TTC TGC TGT GCT TCT GCC CTG    1306
Glu Asn Phe Lys Ala Cys Phe Arg Lys Phe Cys Cys Ala Ser Ala Leu
                325                 330                 335

CAC CGG GAG ATG CAG GTT TCT GAT CGT GTG CGC ACA GTT GCC AAG GAT    1354
His Arg Glu Met Gln Val Ser Asp Arg Val Arg Thr Val Ala Lys Asp
            340                 345                 350

GTA GGC CTT GGT TGC AAG ACC TCT GAG ACA GTA CCA CGG CCG GCA TG     1401
Val Gly Leu Gly Cys Lys Thr Ser Glu Thr Val Pro Arg Pro Ala
        355                 360                 365

ACTAGGCGTG GACCTGCCCA TGGTGCCTGT CAGTCCTAGA GGAAGACCTT TTAGCACCAT  1461

GGGACAGGTC AAAGCATCAA GGTGGCCTCC ATGGCTCTGT CAGATTAAGT TTCCTCCCTG  1521

GTATAGGACC AGAGAGAACC AAAGGAACTG CATGGAAACA TCCACAACTC AGTGGACATG  1581

CCTGGTGAAC CCATGTAGGT ATTCATGGTT CACTTGACTC TTCTCTGGTT TCTCCCTGCT  1641

GCCCTGGTTC TAGGTGGGCT CAGCTGAGGT ATTGTAGTTG TCATGTAGTC ACTATTGTGA  1701

CTACCTGTTG TGTGCTATTG CCCTCAGCCT TCAGTGTTTG CACAGAACTG GTGATCATAC  1761

CCAGTGTTGC CTGGCCCTTA AGCTTGGAGT TGCCTTGGAG CATCTAGTTC TGACTCCACT  1821

GATGCATTCA GATTACCTGA GGTGGGTGAG CATCAGTGGG TTCTTGGATG ACTGTTTCCT  1881

GACGATTCTT TTCATGCTGT ACTATGGTGT ATATGAAGGG GACTTCACAC TTCATCTGGT  1941

ACTGCCACTG CCTGCTCTAC CAACCTGGAC CACCTTCTCA GCAAGAGGCT AGCAGGGGGA  2001

CAAGACACAA AGCTTCCCTA AGGCTCTTTC CCTCCAAAAC CACTGTGAAC TCTTATTCTA  2061

CAGACTGTTT GGCAAGCCCT GCTTCTAACT GTGTGGGAAG TAATCAGGAG AAAATTCTGT  2121

GGCCTCTGTA GGCTGCTCAC AGCATGGAGG CACCACATGC TGGTCTTGGG TATGTGTCTT  2181

GGCTGCTCAG TATGGGCAGG GCAGGGCACG AGACTATCTC TCTCCTTATT CTCCACAGCC  2241
```

```
TCCCTCAGCT CTCCAGCAGT CGCTCTTTTA CTTGACAGTA GAGGTTAGCA GCAGTTGTAC    2301

TCGTAGAAAC ACACTTGTAG CCCGGGAAGA CTGGAGTCAG GATGTGTTCT ATTCTATACC    2361

CACAGTGACC ACCTGCTTCA TTTATAGGGT TAGGACATAT CCAAGCAAGG CCTGGGCTTG    2421

GCATCAAATG AAGAGCTGGT ATGAGAGCTG AAGCCTAAAA TGGCTCATTT GAGCAATCTG    2481

CAAGGACTAT TACGGTTTTG GGGACATTGG AAGAAGAGTC GATACCTTGG AGATATATTG    2541

TTGGTTCACA GAAGAAGAGG CTTTGTAAAT GCCCTTTCTA TGGGTCAGAT AAAAAAAAA    2600
```

(2) INFORMATION FOR SEQ ID NO:2:

(i) SEQUENCE CHARACTERISTICS:
        (A) LENGTH: 367 amino acids
        (B) TYPE: amino acid
        (D) TOPOLOGY: linear (ii) MOLECULE TYPE: protein (xi) SEQUENCE DESCRIPTION: SEQ ID NO:2:

```
Met Glu Ser Leu Phe Pro Ala Pro Phe Trp Glu Val Leu Tyr Gly Ser
  1               5                  10                  15

His Phe Gln Gly Asn Leu Ser Leu Leu Asn Glu Thr Val Pro His His
                 20                  25                  30

Leu Leu Leu Asn Ala Ser His Ser Ala Phe Leu Pro Leu Gly Leu Lys
             35                  40                  45

Val Thr Ile Val Gly Leu Tyr Leu Ala Val Cys Ile Gly Gly Leu Leu
 50                  55                  60

Gly Asn Cys Leu Val Met Tyr Val Ile Leu Arg His Thr Lys Met Lys
 65                  70                  75                  80

Thr Ala Thr Asn Ile Tyr Ile Phe Asn Leu Ala Leu Ala Asp Thr Leu
                 85                  90                  95

Val Leu Leu Thr Leu Pro Phe Gln Gly Thr Asp Ile Leu Leu Gly Phe
            100                 105                 110

Trp Pro Phe Gly Asn Ala Leu Cys Lys Thr Val Ile Ala Ile Asp Tyr
            115                 120                 125

Tyr Asn Met Phe Thr Ser Thr Phe Thr Leu Thr Ala Met Ser Val Asp
130                 135                 140

Arg Tyr Val Ala Ile Cys His Pro Ile Arg Ala Leu Asp Val Arg Thr
145                 150                 155                 160

Ser Ser Lys Ala Gln Ala Val Asn Val Ala Ile Trp Ala Trp Leu Arg
                165                 170                 175

Trp Leu Val Phe Leu Leu Pro Ser Trp Ala Gln His Lys Trp Arg Met
            180                 185                 190

Lys Arg Ser Ser Ala Trp Trp Arg Ser Pro Pro Leu Arg Thr Ile Gly
        195                 200                 205

Ala Leu Tyr Leu Pro Ser Ala Ser Ser Phe Phe Pro Ser Ser Ser Arg
    210                 215                 220

Leu Leu Ile Ile Ser Val Cys Tyr Ser Leu Met Ile Arg Arg Leu Arg
225                 230                 235                 240

Gly Val Arg Leu Leu Ser Gly Ser Arg Glu Lys Asp Arg Asn Leu Arg
                245                 250                 255

Arg Ile Thr Arg Leu Val Leu Val Val Ala Val Phe Val Gly Cys
            260                 265                 270

Trp Thr Pro Val Gln Val Phe Val Leu Val Gln Gly Leu Gly Val Gln
            275                 280                 285
```

```
Pro Gly Ser Glu Thr Ala Val Ala Ile Leu Arg Phe Cys Thr Ala Leu
    290                 295                 300

Gly Tyr Val Asn Ser Cys Leu Asn Pro Ile Leu Tyr Ala Phe Leu Asp
305                 310                 315                 320

Glu Asn Phe Lys Ala Cys Phe Arg Lys Phe Cys Cys Ala Ser Ala Leu
                325                 330                 335

His Arg Glu Met Gln Val Ser Asp Arg Val Arg Thr Val Ala Lys Asp
                340                 345                 350

Val Gly Leu Gly Cys Lys Thr Ser Glu Thr Val Pro Arg Pro Ala
            355                 360                 365

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:3:

GGGCTGTGCA GAAGCGCAGA                                              20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:4:

CCCGACACGT CTTCGCGTCT                                              20

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:5:

GGGTCGTGCA GAGACGCAGA                                              20
```

What is claimed is:

1. An isolated polynucleotide that encodes a mammalian KOR-3 receptor comprising an amino acid residue sequence of sequence SEQ ID NO: 2.

2. The polynucleotide of claim 1, wherein the polynucleotide is a DNA molecule.

3. The polynucleotide of claim 1, wherein the polynucleotide is an RNA molecule.

4. A polynucleotide composition comprising an RNA molecule that is complementary to the RNA molecule of claim 3.

5. An isolated polynucleotide that encodes a mammalian KOR-3 receptor, wherein the polynucleotide comprises the nucleotide base sequence of SEQ ID NO: 1.

6. An expression vector comprising a polynucleotide that encodes a mammalian KOR-3 receptor comprising an amino acid residue sequence of sequence SEQ ID NO: 2.

7. The expression vector of claim 6, wherein said polynucleotide is a DNA molecule comprising a nucleotide base sequence of SEQ ID NO: 1.

8. The expression vector of claim 7, wherein the nucleotide base sequence of sequence SEQ ID NO: 1 is operatively linked to an enhancer and/or promoter.

9. A transformed host cell comprising a polynucleotide that encodes a mammalian KOR-3 receptor polypeptide, wherein the polynucleotide comprises the nucleotide base sequence of SEQ ID NO: 1.

10. The transformed host cell of claim 9, wherein the polynucleotide is introduced into the cell by transfection, electroporation or transformation of the cell with a vector comprising the polynucleotide.

11. The transformed host cell of claim 9, wherein the host cell expresses the polynucleotide to produce the encoded mammalian KOR-3 receptor polypeptide.

12. A process for preparing a transformed host cell expressing a mammalian KOR-3 receptor polypeptide comprising the steps of:
   a) transfecting, electroporating or transforming a cell with a polynucleotide that encodes a mammalian KOR-3 receptor polypeptide comprising an amino acid residue sequence of SEQ ID NO: 2 to produce a transformed host cell; and
   b) maintaining the transformed host cell under biological conditions sufficient for expression of said mammalian KOR-3 receptor polypeptide in the host cell.

13. A process for preparing a transformed host cell expressing a mammalian KOR-3 receptor polypeptide comprising the steps of:
   a) transfecting, electroporating or transforming a cell with a polynucleotide that encodes a mammalian KOR-3 receptor polypeptide, wherein the polynucleotide is a DNA molecule comprising a nucleotide base sequence of SEQ ID NO: 1, to produce a transformed host cell; and
   b) maintaining the transformed host cell under biological conditions sufficient for expression of said mammalian KOR-3 receptor polypeptide in the host cell.

14. The vector of claim 7, wherein the vector is 13-2A4 (ATCC Accession No. 75608).

15. A polynucleotide encoding a KOR-3 receptor wherein said polynucleotide is at least 95% homologous to SEQ ID NO: 1 and wherein the encoded receptor binds OFQ/nociceptin.

16. A process for preparing a transformed host cell expressing a mammalian KOR-3 receptor polypeptide comprising the steps of:
   a) transfecting, electroporating or transforming a cell with the KOR-3 receptor-encoding polynucleotide of claim 18, to produce a transformed host cell; and
   b) maintaining the transformed host cell under biological conditions sufficient for expression of said mammalian KOR-3 receptor polypeptide in the host cell.

17. A transformed host cell comprising the KOR-3 receptor-encoding polynucleotide of claim 15.

18. A polynucleotide encoding a KOR-3 receptor wherein said receptor is at least 95% homologous to SEQ ID NO: 2 and wherein the encoded receptor binds OFQ/nociceptin.

19. A process for preparing a cell expressing a mammalian KOR-3 receptor polypeptide comprising the steps of:
   a) transfecting, electroporating or transforming a cell with the KOR-3 receptor-encoding the polynucleotide of claim 18, to produce a transformed host cell; and
   b) maintaining the transformed host cell under biological conditions sufficient for expression of said mammalian KOR-3 receptor polypeptide in the host cell.

20. A transformed host cell comprising the KOR-3 receptor-encoding polynucleotide of claim 18.

21. An expression vector comprising the polynucleotide of claim 15.

22. An expression vector comprising the polynucleotide of claim 18.

23. A method of preparing an opioid receptor comprising the steps of:
   a) introducing the polynucleotide of any one of claim 1, 5, 15, or 18 into a host cell; and
   b) growing the host cell under conditions such that the polynucleotide is expressed,
thereby preparing an opioid receptor.

* * * * *

UNITED STATES PATENT AND TRADEMARK OFFICE
CERTIFICATE OF CORRECTION

PATENT NO.   : 6,660,496 B1
DATED        : December 9, 2003
INVENTOR(S)  : Pasternak et al.

It is certified that error appears in the above-identified patent and that said Letters Patent is hereby corrected as shown below:

Columns 21 to 28,
Kindly replace the Sequence Listing with the enclosed copy.

Column 30,
Lines 18-19, kindly change "the KOR-3 receptor-encoding polynucleotide of claim 18" to -- the KOR-3 receptor encoding polynucleotide of claim 15 --.

Signed and Sealed this

Twenty-third Day of March, 2004

JON W. DUDAS
*Acting Director of the United States Patent and Trademark Office*

SEQUENCE LISTING

<110> Sloan-Kettering Institute for Cancer Research
      Pasternak, Gavril W
      Pan, Ying-Xian <120> NUCLEIC ACID MOLECULES ENCODING KAPPA OPIOID RECEPTORS, RECEPTORS ENCODED THEREBY, AND USES THEREOF

<130> 830002-2004

<140> 09/986,209
<141> 1997-12-05

<160> 5

<170> PatentIn version 3.1

<210> 1
<211> 2600
<212> DNA
<213> Mus musculus

<220>
<221> CDS
<222> (299)..(1402)
<223>

<400> 1

```
tttggcttcc ttctccaacc tgcgcagccc ctccttctct cagccgcagc cttctgcccc      60 tccccettct ggctgccgca ctggctgctg cgtctagtca atatcttatc ttcggagcag     120
gagctaggag ccattcccag ccggagcaga ccccaagcta gagtgagaag cattactcag     180
ttcattgtgc tcctgcctgc ctttctgcta agcattaggg tctgttttgg cccagcttct     240
gaagaggttg tgtgtgctgt tggaggaact gtactgagtg gctttgcagg gtgacagc      298 atg gag tcc ctc ttt cct gcc cca ttc tgg gag gtc ttg tat ggc agc      346
Met Glu Ser Leu Phe Pro Ala Pro Phe Trp Glu Val Leu Tyr Gly Ser
1               5                  10                  15 cac ttt caa ggg aac ctg tct ctc cta aat gag acc gta ccc cat cac      394
His Phe Gln Gly Asn Leu Ser Leu Leu Asn Glu Thr Val Pro His His
                20                  25                  30 ctg ctc ctc aat gct agc cac agt gcc ttc ctg ccc ctt gga ctc aag      442
Leu Leu Leu Asn Ala Ser His Ser Ala Phe Leu Pro Leu Gly Leu Lys
            35                  40                  45 gtc acc atc gtg ggg ctc tac ttg gct gtg tgc atc ggg ggg ctc ctg      490
Val Thr Ile Val Gly Leu Tyr Leu Ala Val Cys Ile Gly Gly Leu Leu
        50                  55                  60 ggg aac tgc ctc gtc atg tat gtc atc ctc agg cac acc aag atg aag      538
```

```
Gly Asn Cys Leu Val Met Tyr Val Ile Leu Arg His Thr Lys Met Lys
65                  70                  75                  80 act gct acc aac att tac ata ttt aat ctg gca ctg gct gat acc ctg    586
Thr Ala Thr Asn Ile Tyr Ile Phe Asn Leu Ala Leu Ala Asp Thr Leu
                85                  90                  95 gtc ttg ctg aca ctg ccc ttc cag ggc aca gac atc ctt ctg ggc ttc    634
Val Leu Leu Thr Leu Pro Phe Gln Gly Thr Asp Ile Leu Leu Gly Phe
            100                 105                 110 tgg cca ttt ggg aat gca ctg tgc aag acg gtc att gct atc gac tac    682
Trp Pro Phe Gly Asn Ala Leu Cys Lys Thr Val Ile Ala Ile Asp Tyr
        115                 120                 125 tac aac atg ttt acc agc act ttc act ttg act gcc atg agt gta gac    730
Tyr Asn Met Phe Thr Ser Thr Phe Thr Leu Thr Ala Met Ser Val Asp
    130                 135                 140 cgt tat gta gct atc tgc cac cct atc cgt gcc ctt gat gtt cgg aca    778
Arg Tyr Val Ala Ile Cys His Pro Ile Arg Ala Leu Asp Val Arg Thr
145                 150                 155                 160 tcc agt aaa gcc cag gcc gtt aat gtg gcc ata tgg gcc ctg gct tcg    826
Ser Ser Lys Ala Gln Ala Val Asn Val Ala Ile Trp Ala Leu Ala Ser
                165                 170                 175 gtg gtt ggt gtt cct gtt gcc atc atg ggc tca gca caa gtg gag gat    874
Val Val Gly Val Pro Val Ala Ile Met Gly Ser Ala Gln Val Glu Asp
            180                 185                 190 gaa gag atc gag tgc ctg gtg gag atc ccc gcc cct cag gac tat tgg    922
Glu Glu Ile Glu Cys Leu Val Glu Ile Pro Ala Pro Gln Asp Tyr Trp
        195                 200                 205 ggc cct gta ttt gcc atc tgc atc ttc ctt ttt tcc ttc atc atc ccg    970
Gly Pro Val Phe Ala Ile Cys Ile Phe Leu Phe Ser Phe Ile Ile Pro
    210                 215                 220 gtt ctg atc atc tct gtc tgc tac agc ctc atg att cga cga ctt cgt    1018
Val Leu Ile Ile Ser Val Cys Tyr Ser Leu Met Ile Arg Arg Leu Arg
225                 230                 235                 240 ggt gtc cgg ctg ctt tca ggc tcc cga gag aag gac cgg aac ctg cga    1066
Gly Val Arg Leu Leu Ser Gly Ser Arg Glu Lys Asp Arg Asn Leu Arg
                245                 250                 255 cgc atc aca cgg ctg gta ctg gta gtt gtg gct gtg ttt gtg ggc tgc    1114
Arg Ile Thr Arg Leu Val Leu Val Val Ala Val Phe Val Gly Cys
            260                 265                 270 tgg aca cct gtg cag gtc ttt gtc ctg gtt caa gga ctg ggt gtt cag    1162
Trp Thr Pro Val Gln Val Phe Val Leu Val Gln Gly Leu Gly Val Gln
        275                 280                 285 cca ggt agt gag act gca gta gcc att ctg cgc ttc tgc aca gcc ctg    1210
Pro Gly Ser Glu Thr Ala Val Ala Ile Leu Arg Phe Cys Thr Ala Leu
```

```
              290                     295                     300
ggc tat gtc aac agt tgt ctc aat ccc att ctc tat gct ttc ttg gat    1258
Gly Tyr Val Asn Ser Cys Leu Asn Pro Ile Leu Tyr Ala Phe Leu Asp
305                 310                 315                 320 gag aac ttc aag gcc tgc ttt aga aag ttc tgc tgt gct tct gcc ctg    1306
Glu Asn Phe Lys Ala Cys Phe Arg Lys Phe Cys Cys Ala Ser Ala Leu
                325                 330                 335 cac cgg gag atg cag gtt tct gat cgt gtg cgc agc att gcc aag gat    1354
His Arg Glu Met Gln Val Ser Asp Arg Val Arg Ser Ile Ala Lys Asp
            340                 345                 350 gta ggc ctt ggt tgc aag acc tct gag aca gta cca cgg ccg gca tga    1402
Val Gly Leu Gly Cys Lys Thr Ser Glu Thr Val Pro Arg Pro Ala
                355                 360                 365 ctaggcgtgg acctgcccat ggtgcctgtc agtcctagag aagacctttt agcaccatg   1462
ggacaggtca aagcatcaag gtggcctcca tggctctgtc agattaagtt tcctccctgg   1522
tataggacca gagagaacca aaggaactgc atggaaacat ccacaactca gtggacatgc   1582
ctggtgaacc catgtaggta ttcatggttc acttgactct tctctggttt ctccctgctg   1642
ccctggttct aggtgggctc agctgaggta ttgtagttgt catgtagtca ctattgtgac   1702
tacctgttgt gtgctattgc cctcagcctt cagtgtttgc acagaactgg tgatcatacc   1762
cagtgttgcc tggcccttaa gcttggagtt gccttggagc atctagttct gactccactg   1822
atgcattcag attacctgag gtgggtgagc atcagtgggt tcttggatga ctgtttcctg   1882
acgattcttt tcatgctgta ctatggtgta tatgaagggg acttcacact tcatctggta   1942
ctgccactgc ctgctctacc aacctggacc accttctcag caagaggcta gcaggggac    2002
aagacacaaa gcttccctaa ggctctttcc ctccaaaacc actgtgaact cttattctac   2062
agactgtttg gcaagccctg cttctaactg tgtgggaagt aatcaggaga aaattctgtg   2122
gcctctgtag gctgctcaca gcatggaggc accacatgct ggtcttgggt atgtgtcttg   2182
gctgctcagt atgggcaggg cagggcacga gactatctct ctccttattc tccacagcct   2242
ccctcagctc tccagcagtc gctcttttac ttgacagtag aggttagcag cagttgtact   2302
cgtagaaaca cacttgtagc ccgggaagac tggagtcagg atgtgttcta ttctataccc   2362
acagtgacca cctgcttcat ttatagggtt aggacatatc caagcaaggc ctgggcttgg   2422
catcaaatga agagctggta tgagagctga agcctaaaat ggctcatttg agcaatctgc   2482
aaggactatt acggttttgg ggacattgga agaagagtcg ataccttgga gatatattgt   2542
tggttcacag aagaagaggc tttgtaaatg ccctttctat gggtcagata aaaaaaaa    2600
```

```
<210>  2
<211>  367
<212>  PRT
<213>  Mus musculus

<400>  2
```

| | | | | | | | | | | | | | | |
|---|---|---|---|---|---|---|---|---|---|---|---|---|---|---|
|Met|Glu|Ser|Leu|Phe|Pro|Ala|Pro|Phe|Trp|Glu|Val|Leu|Tyr|Gly|Ser|
|1| | | |5| | | | |10| | | | |15|

| | | | | | | | | | | | | | | |
|---|---|---|---|---|---|---|---|---|---|---|---|---|---|---|
|His|Phe|Gln|Gly|Asn|Leu|Ser|Leu|Asn|Glu|Thr|Val|Pro|His|His|
| | | |20| | | |25| | | |30| | | |

|Leu|Leu|Leu|Asn|Ala|Ser|His|Ser|Ala|Phe|Leu|Pro|Leu|Gly|Leu|Lys|
|---|---|---|---|---|---|---|---|---|---|---|---|---|---|---|---|
| | |35| | | |40| | | |45| | | | | |

|Val|Thr|Ile|Val|Gly|Leu|Tyr|Leu|Ala|Val|Cys|Ile|Gly|Gly|Leu|Leu|
|---|---|---|---|---|---|---|---|---|---|---|---|---|---|---|---|
| |50| | | | |55| | | |60| | | | | |

|Gly|Asn|Cys|Leu|Val|Met|Tyr|Val|Ile|Leu|Arg|His|Thr|Lys|Met|Lys|
|---|---|---|---|---|---|---|---|---|---|---|---|---|---|---|---|
|65| | | | |70| | | |75| | | | |80| |

|Thr|Ala|Thr|Asn|Ile|Tyr|Ile|Phe|Asn|Leu|Ala|Leu|Ala|Asp|Thr|Leu|
|---|---|---|---|---|---|---|---|---|---|---|---|---|---|---|---|
| | | | |85| | | | |90| | | | |95| |

|Val|Leu|Leu|Thr|Leu|Pro|Phe|Gln|Gly|Thr|Asp|Ile|Leu|Leu|Gly|Phe|
|---|---|---|---|---|---|---|---|---|---|---|---|---|---|---|---|
| | | |100| | | | |105| | | | |110| | |

|Trp|Pro|Phe|Gly|Asn|Ala|Leu|Cys|Lys|Thr|Val|Ile|Ala|Ile|Asp|Tyr|
|---|---|---|---|---|---|---|---|---|---|---|---|---|---|---|---|
| | |115| | | | |120| | | | |125| | | |

|Tyr|Asn|Met|Phe|Thr|Ser|Thr|Phe|Thr|Leu|Thr|Ala|Met|Ser|Val|Asp|
|---|---|---|---|---|---|---|---|---|---|---|---|---|---|---|---|
| |130| | | | |135| | | | |140| | | | |

|Arg|Tyr|Val|Ala|Ile|Cys|His|Pro|Ile|Arg|Ala|Leu|Asp|Val|Arg|Thr|
|---|---|---|---|---|---|---|---|---|---|---|---|---|---|---|---|
|145| | | | |150| | | | |155| | | | |160|

|Ser|Ser|Lys|Ala|Gln|Ala|Val|Asn|Val|Ala|Ile|Trp|Ala|Leu|Ala|Ser|
|---|---|---|---|---|---|---|---|---|---|---|---|---|---|---|---|
| | | | |165| | | | |170| | | | |175| |

|Val|Val|Gly|Val|Pro|Val|Ala|Ile|Met|Gly|Ser|Ala|Gln|Val|Glu|Asp|
|---|---|---|---|---|---|---|---|---|---|---|---|---|---|---|---|
| | | |180| | | | |185| | | | |190| | |

```
Glu Glu Ile Glu Cys Leu Val Glu Ile Pro Ala Pro Gln Asp Tyr Trp
        195                 200                 205

Gly Pro Val Phe Ala Ile Cys Ile Phe Leu Phe Ser Phe Ile Ile Pro
        210                 215                 220

Val Leu Ile Ile Ser Val Cys Tyr Ser Leu Met Ile Arg Arg Leu Arg
225                 230                 235                 240

Gly Val Arg Leu Leu Ser Gly Ser Arg Glu Lys Asp Arg Asn Leu Arg
                245                 250                 255

Arg Ile Thr Arg Leu Val Leu Val Val Ala Val Phe Val Gly Cys
        260                 265                 270

Trp Thr Pro Val Gln Val Phe Val Leu Val Gln Gly Leu Gly Val Gln
        275                 280                 285

Pro Gly Ser Glu Thr Ala Val Ala Ile Leu Arg Phe Cys Thr Ala Leu
        290                 295                 300

Gly Tyr Val Asn Ser Cys Leu Asn Pro Ile Leu Tyr Ala Phe Leu Asp
305                 310                 315                 320

Glu Asn Phe Lys Ala Cys Phe Arg Lys Phe Cys Cys Ala Ser Ala Leu
                325                 330                 335

His Arg Glu Met Gln Val Ser Asp Arg Val Arg Ser Ile Ala Lys Asp
        340                 345                 350

Val Gly Leu Gly Cys Lys Thr Ser Glu Thr Val Pro Arg Pro Ala
        355                 360                 365

<210>   3
<211>   20
<212>   DNA
<213>   artificial sequence

<220>
<223>   Antisense oligodeoxynucleotide designed for testing of kappa3 opi
        oid receptor clone <400>   3
gggctgtgca gaagcgcaga                                              20
```

```
<210>  4
<211>  20
<212>  DNA
<213>  artificial sequence

<220>
<223>  Complementary sense strand to oligodeoxynucleotide designed for t
       esting of kappa 3 opioid receptor clone <400>  4
cccgacacgt cttcgcgtct                                                    20

<210>  5
<211>  20
<212>  DNA
<213>  artificial sequence

<220>
<223>  Mismatched antisense strand of oligodeoxynucleotide designed for
       testing of kappa 3 opioid receptor clone <400>  5
gggtcgtgca gagacgcaga                                                    20
```